United States Patent
Dupont-Passelaigue et al.

(10) Patent No.: US 9,156,834 B2
(45) Date of Patent: Oct. 13, 2015

(54) DERIVATIVES OF HETEROARYLSULFONAMIDES, THEIR PREPARATION AND THEIR APPLICATION IN HUMAN THERAPY

(71) Applicant: PIERRE FABRE MEDICAMENT, Boulogne-Billancourt (FR)

(72) Inventors: Elisabeth Dupont-Passelaigue, Colomiers (FR); Isabelle Le Roy, Frouzins (FR); Christophe Pignier, Castres (FR)

(73) Assignee: PIERRE FABRE MEDICAMENT, Boulogne-Billancourt (FR)

( * ) Notice: Subject to any disclaimer, the term of this patent is extended or adjusted under 35 U.S.C. 154(b) by 0 days.

(21) Appl. No.: 14/460,951

(22) Filed: Aug. 15, 2014

(65) Prior Publication Data

US 2014/0357624 A1    Dec. 4, 2014

Related U.S. Application Data

(62) Division of application No. 13/822,406, filed as application No. PCT/EP2011/070736 on Nov. 23, 2011, now Pat. No. 8,846,930.

(30) Foreign Application Priority Data

Nov. 23, 2010 (FR) .................................. 10 59634

(51) Int. Cl.
| | | |
|---|---|---|
| C07D 413/14 | (2006.01) |
| C07D 413/12 | (2006.01) |
| C07D 417/14 | (2006.01) |
| C07D 419/00 | (2006.01) |
| C07D 413/00 | (2006.01) |
| C07D 417/12 | (2006.01) |
| C07D 417/00 | (2006.01) |
| C07D 261/20 | (2006.01) |
| A61K 31/497 | (2006.01) |
| A61K 31/445 | (2006.01) |
| A01N 43/40 | (2006.01) |

(52) U.S. Cl.
CPC ............ *C07D 417/14* (2013.01); *C07D 413/12* (2013.01); *C07D 413/14* (2013.01); *C07D 417/12* (2013.01)

(58) Field of Classification Search
USPC ........................................ 514/338; 546/270.1
See application file for complete search history.

(56) References Cited

U.S. PATENT DOCUMENTS

| | | |
|---|---|---|
| 5,149,700 A | 9/1992 | Ellingboe et al. |
| 7,235,664 B2 | 6/2007 | Brendel et al. |
| 7,241,761 B2 | 7/2007 | Jolidon et al. |
| 2010/0331307 A1 | 12/2010 | Salituro et al. |

FOREIGN PATENT DOCUMENTS

| | | |
|---|---|---|
| EP | 1 939 189 A1 | 7/2008 |
| WO | WO 2006/130986 A1 | 12/2006 |
| WO | WO 2009/055357 A1 | 4/2009 |
| WO | WO 2009/149508 A1 | 12/2009 |
| WO | WO 2010/023445 | 3/2010 |
| WO | WO 2010/111948 A1 | 10/2010 |
| WO | WO 2010/130638 | 11/2010 |

OTHER PUBLICATIONS

Wulff; Nat. Rev. Drug. Discov. 2009, 8, 982-1001.*
Bhakta et al., "Pharmacologic targets for atrial fibrillation," Expert Opin. Ther. Targets, vol. 11, No. 9, 2007, pp. 1161-1178.
Blackiston et al., "Bioelectric controls of cell proliferation: Ion channels, membrane voltage and the cell cycle," Cell Cycle, vol. 8, No. 21, Nov. 1, 2009, pp. 3519-3528. (NIH Public Access Author Manuscript, 24 pages).
Gogelein et al., "Effects of the atrial antiarrhythmic drug AVE0118 on cardiac ion channels," Naunyn-Schmiedeberg's Arch Pharmacol, vol. 370, 2004, pp. 183-192.
Gutman et al., "International Union of Pharmacology. LIII. Nomenclature and Molecular Relationships of Voltage-Gated Potassium Channels," Pharmacol Rev, vol. 57, No. 4, 2005, pp. 473-508.
International search report issued in PCT/EP2011/070736 mailed Jan. 19, 2012.
Miyasaka et al., "Secular Trends in Incidence of Atrial Fibrillation in Olmsted County, Minnesota, 1980 to 2000, and Implications on the Projections for Future Prevalence," Circulation, vol. 114, 2006, pp. 119-125.
Nerbonne et al., "Molecular Physiology of Cardiac Repolarization," Physiol Rev., vol. 85, 2005, pp. 1205-1253.

(Continued)

*Primary Examiner* — John Mabry
*Assistant Examiner* — Daniel Carcanague
(74) *Attorney, Agent, or Firm* — Birch, Stewart, Kolasch & Birch, LLP

(57) ABSTRACT

The present invention concerns derivatives of heteroarylsulfonamides, notably as blockers of Kv potassium channels, and more particularly of channels Kv1.5, Kv4.3 or Kv11.1, their application in clinical therapy and their preparation methods. These compounds correspond to the following general formula (I): where R1 represents one or more substituents of the phenyl core X such as: hydrogen, halogen, trifluoromethyl, trifluoromethoxy, linear or branched $C_1$-$C_4$ alkyl, or linear or branched $C_1$-$C_4$ alkoxy, A represents oxygen or sulphur, B represents nitrogen when n=1 or 2 and D represents —C(=O)—, or B represents CH when n=0 and D represents —$CH_2$O— or when n=1 and D represents —O—, R2 represents a hydrogen, a methyl, a fluorine or chlorine atom or a methoxy, HetAr represents a pyridyl or quinolyl group, possibly substituted by a group such as a linear or branched $C_1$-$C_4$ alkyl, a linear or branched $C_1$-$C_4$ alkoxy, a halogen, or a trifluoromethyl, and to their pharmaceutically acceptable salts.

9 Claims, No Drawings

(56) References Cited

OTHER PUBLICATIONS

Page et al., "Drug Therapy for Atrial Fibrillation: Where Do We Go From Here?," Nature Reviews, vol. 4, Nov. 2005, pp. 899-910.

Pardo et al., "Role of Voltage-gated Potassium Channels in Cancer," J. Membrane Biol., vol. 205, 2005, pp. 115-124.

Pardo, "Voltage-Gated Potassium Channels in Cell Proliferation," Physiology, vol. 19, 2004, pp. 285-292.

Regan et al., "Atrial Antifibrillatory Effects of Structurally Distinct I Kur Blockers 3-[(Dinnethylamino)methy1]-6-methoxy-2-methyl-4-Phenylisoquinolin . . . ," The Journal of Pharmacology and Experimental Therapeutics, vol. 324, No. 1, 2008, pp. 322-330.

Tamargo et al., "Pharmacology of cardiac potassium channels," Cardiovascular Research, vol. 62, 2004, pp. 9-33.

Wermuth; Practice of Medicinal Chemistry, Third Ed. 2008, Elsevier, chapters 6 and 15.

Wirth et al., "Atrial effects of the novel K+-channel-blocker AVE0118 in anesthetized pigs," Cardiovascular Research, vol. 60, 2003, pp. 298-306.

* cited by examiner

DERIVATIVES OF HETEROARYLSULFONAMIDES, THEIR PREPARATION AND THEIR APPLICATION IN HUMAN THERAPY

CROSS REFERENCE TO RELATED APPLICATIONS

This application is a Divisional of copending application Ser. No. 13/822,406, filed on Mar. 12, 2013, which was filed as PCT International Application No. PCT/EP2011/070736 on Nov. 23, 2011, which claims the benefit under 35 U.S.C. §119(a) to Patent Application No. 1059634, filed in France on Nov. 23, 2010, all of which are hereby expressly incorporated by reference into the present application.

The present invention concerns derivatives of heteroarylsulfonamides, their preparation and their applications in human therapy, as blockers of Kv potassium channels and specifically channels Kv1.5, Kv4.3 and Kv11.1.

Potassium channels represent the largest family of ion channels in the human genome, with approximately 80 genes (Tamargo et al., Cardiovasc. Res. 2004, 62: 9-33). These potassium channels can be subdivided into 3 sub-families: channels activated by potential or voltage (4 channels) and calcium ($K_{Ca}$ channels), inward rectifier channels ($K_{ir}$) and two-pore potassium channels ($K_{2p}$). The sub-family of voltage-activated channels is the one most represented in the human organism, with an almost ubiquitous distribution in excitable cells (cardiac cells, neurons, striated or smooth muscle cells) and non-excitable cells such as pancreatic, prostatic, parathyroid cells, etc. (for review, Gutman G et al., Pharmacol. Rev. 2005, 57:473-508).

The main function of the Kv potassium channels in excitable cells is the control of the resting membrane potential and of the action potential duration (Nerbonne and Kass, Physiol. Rev. 2005, 85:1205-1253). As such, several Kv channels are involved in this control, in both the heart auricles and ventricles. The Kv4.3 channels associated with the KChIP 2 sub-units form the current $I_{to}$ which is involved in the premature repolarisation phase of the action potential (PA), the KVLQT1/MinK and hERG channels which are involved in the late repolarisation phase of the PA (generating respectively currents $I_{Ks}$ and $I_{Kr}$). The abovementioned channels are distributed uniformly between the heart auricles and ventricles. However, two other types of potassium channels show a distribution only in the auricles. The potential-dependent potassium channels ($K_{v1.5}$) responsible for the current $I_{Kur}$ and the acetylcholine-activated inward rectifier channels (Kir3.1 and Kir3.4 responsible for current $I_{K-Ach}$).

Modifications of the membranous electrical activity are observed in many pathologies, notably heart rhythm disorder pathologies. Among the latter, atrial fibrillation (FA) is a serious rhythm disorder which corresponds to totally desynchronised activity of the atrial myocytes resulting in interrupted, rapid and irregular electrical activity. FA is caused by the appearance of electrical reentry circuits in the atrial tissue (Miyasaka Y et al., Circulation 2006, 114:119-125). There is currently no specific anti-arhythmic treatment of the atrial stage to reduce the incidence of FA, which therefore constitutes an important medical need (Page and Roden, Nat. Rev. Drug Discov. 2005, 4:899-910).

The presence of many simultaneously activated microreentry circuits explains the anarchic character of the electrical activity observed either by intracavitary means or in electrocardiograms. This rhythmic disorder generally develops on a pathological atrial myocardium in electrophysiological terms, the refractory periods of which are too short and too unequal, and therefore very vulnerable to the smallest extrasystole. These anomalies form part of a phenomenon of myocardial remodelling, following a pressure overload or a stretching causing morphological alterations (hypertrophy, dilatation, fibrosis), as well as modifications in the regulation of the trans-membranous ionic currents, modifying the electrophysiological characteristics of the atrial myocytes. Given that each FA access maintains, or aggravates, this mechanical and electrophysiological remodelling process, it will be understood that FA has a great potential risk of recurrence, and that its natural development is towards chronicity. Conversely, focal-type FAs have recently been identified, originating in a precise point, which is almost always found to be an extension of the atrial myocardium in the pulmonary veins.

These quite rare cases of FA have a quite monomorphous character, and in any event one which is comparable to that of atrial extrasystoles initiating access, or observed intermittently between crises. In all cases, the consequence of the loss of the atrial systole is a reduction in the heart rate of between 20 and 30%, and higher the more the rate is reduced to the basal state. Simultaneously, the existence of blood stasis in the atrial cavities, notably in certain pockets such as the auricles, accounts for the thromboembolic risk. However, the embolic risk is only partially conditional on the presence of the FA alone, since atrial stasis is also related to the increase of intracavitary pressures (systolic or diastolic left ventricular dysfunction, valvular heart disease or valve replacement).

Electrical remodelling therefore constitutes the major substrate of the genesis of the FA; it results from a diminution of the activity of the L-type calcic channels allowing the Kv1.5 potassium channels to play fully their repolarising role through the ultra-rapid potassium current (Bhakta and Miller, Expert Opin. Ther. Targets 2007, 11:1161-1178). Its consequence is a dramatic shortening of the refractory period, which constitutes the triggering factor of micro-reentries. Bearing in mind that the Kv1.5 potassium channels are not expressed functionally in the ventricular stage, a blocker of these channels will therefore constitute a selected anti-arhythmic of the atrial stage without affecting the ventricular electrophysiology. Its pharmacological effect takes the form of a lengthening of the refractory period, and therefore a lesser incidence of micro-reentry circuits. A quantity of experimental data obtained with reference products confirms the interest of the blockage of Kv1.5 as a therapeutic target (Gögelein et al., Naunyn Schmiedeberg's Arch. Pharmacol. 2004, 370:183-192; Regan et al., J. Pharmacol. Exp. Ther. 2008, 324:322-330).

Rapid changes of membrane potential are well-known in excitable cells, but slow variations of potential are observed in all the cells and are associated with the control of the cell cycle. The cell cycle is a key parameter in cell behaviour, which must be regulated and coordinated for development, tissue regeneration and cell proliferation (Pardo, Physiology, 2004, 19:285-292; Blackistion et al., Cell Cycle, 2009, 8-21: 3527-3536). Generally speaking, the blockage of the potassium channels leads to reduced proliferation in physiological models (as in lymphocytes) and pathological models (cancer). The role of the potassium channels in regulating the cell cycle has been demonstrated in many cell types, whether physiological or pathological (cancer cell lines or tumours) originating from human melanoma, lung cancer, lymphoma, mesothelioma, hepatocellular carcinoma, lymphocytes, monocytes (for review Pardo et al., J. Membr. Biol, 2005, 205:115-124).

As used previously, the term "Kv" indicates the family of voltage-dependent potassium channels, and includes various sub-families (Kv1, Kv2, Kv3, etc.) among which are the Kv1.1, Kv1.2, Kv1.3 channels, . . . "A blacker of the Kv channels" denotes a molecule which reduces or blocks the K⁺ ion flow through the channel.

As used here, the term "salts" designates acid or base addition salts, notably mineral ones, of the compounds of the present invention, and notably base addition salts using bases such as LION, KOH or NaOH or acid addition salts using acids such as HCl. The salts are preferably pharmaceutically acceptable, i.e. they are non-toxic for the patient to whom they are administered. The term "pharmaceutically acceptable" refers to molecular entities and compositions producing no adverse or allergic effect, or other undesirable reaction when administered to an animal or a human. When used here, the term "pharmaceutically acceptable excipient" includes all diluents, additives or excipients, such as preservative agents, fillers, disintegrating agents, wetting agents, emulsifiers, dispersants, anti-bacterials or antifungals, or also agents allowing intestinal and digestive absorption and resorption to be slowed. The use of these media or vectors is well-known in the art. Unless the agent is chemically incompatible with a derivative of heteroarylsulfonamides its use in pharmaceutical compositions with the compounds according to the invention is envisaged. In the context of the invention, the term "treatment", as used here, means inhibiting the occurrence or progress of the affection to which the term applies, or one or more symptoms of this affection.

The purpose of the present invention is derivatives of heteroarylsulfonamides which are blockers of the Kv potassium channels (more specifically the Kv1.5, Kv4.3 and Kv11.1 channels) and their application in clinical therapy.

These compounds have the following general formula I:

I where
R1 represents one or more substituents of the phenyl core X chosen from among the group consisting of: hydrogen, halogen (such as F, Cl, Br), trifluoromethyl, trifluoromethoxy, linear or branched $C_1$-$C_4$ alkyl, and linear or branched $C_1$-$C_4$ alkoxy,
n represents 0, 1 or 2,
A represents oxygen or sulphur,
D represents —C(=O)—, —CH₂O— or —O—,
B represents nitrogen when n=1 or 2 and D represents —C(=O)—,
or B represents CH when n=0 and D represents —CH₂O— or when n=1 and D represents —O—,
R2 represents a hydrogen, a methyl, a fluorine or chlorine atom or a methoxy,
HetAr represents a pyridyl or quinolyl group, possibly substituted by a group such as a linear or branched $C_1$-$C_4$ alkyl, a linear or branched $C_1$-$C_4$ alkoxy, a halogen (such as F, Cl, Br), or trifluoromethyl,
as well as their pharmaceutically acceptable salts.

The sulfonamide group (—NH—SO₂HetAr) can be located on the phenyl core Y in ortho, meta or para of the position occupied by group D.

"Linear or branched $C_1$-$C_4$ alkyl" means, in the sense of the present invention, a linear or branched hydrocarbon chain, including 1 to 4 carbon atoms, such as the methyl, ethyl, n-propyl, isopropyl, n-butyl, sec-butyl, isobutyl and tert-butyl groups.

"Linear or branched $C_1$-$C_4$ alkoxy", means, in the sense of the present invention, a linear or branched $C_1$-$C_4$ alkyl group as defined above linked to the remainder of the molecule through an oxygen atom, such as the methoxy, ethoxy, n-propoxy, isopropoxy, n-butoxy, sec-butoxy, isobutoxy and tert-butoxy groups.

According to an embodiment of the invention, the compounds of general formula I are those matching the following formula (Ia):

Ia where R1, R2, A, B, D, n and HetAr are as defined above, as well as their pharmaceutically acceptable salts.

According to another embodiment of the invention, compounds of general formula I or Ia are those for which:
R1 represents one or more substituents of the phenyl core X chosen from among the group consisting of: hydrogen, halogen (such as F, Cl, Br), trifluoromethyl, trifluoromethoxy, linear or branched $C_1$-$C_4$ alkyl, and methoxy,
n represents 1,
A represents oxygen or sulphur,
D represents —C(=O)— or —O—,
B represents nitrogen when D represents —C(=O)—,
or B represents CH when D represents —O—,
R2 represents a hydrogen,
HetAr represents a 2-pyridyl or 8-quinolyl group, possibly substituted by a group such as methyl or trifluoromethyl,
and the sulfonamide group (—NH—SO₂HetAr) is notably located on the phenyl core Y in ortho of the position occupied by group D,
as well as their pharmaceutically acceptable salts.

According to another embodiment of the invention, compounds of general formula I or Ia are those for which:
R1 represents one or more substituents of the phenyl group X chosen from among the group consisting of: hydrogen, halogen (such as F, Cl, Br), trifluoromethyl, trifluoromethoxy, linear or branched $C_1$-$C_4$ alkyl, and methoxy,
A represents sulphur,
n represents 1,
D represents —C(=O)—,
B represents nitrogen,
R2 represents a hydrogen,
HetAr represents a 2-pyridyl group, possibly substituted by a group such as methyl or trifluoromethyl,
and the sulfonamide group (—NH—SO₂HetAr) is located on the phenyl core Y in ortho of the position occupied by group D,
as well as their pharmaceutically acceptable salts.

The present invention concerns the compounds of general formula I characterised in that they are chosen from among:

1) N-(2-(4-(6-fluorobenzo[d]oxazol-2-yl)piperazine-1-carbonyl)phenyl)-5-(trifluoromethyl)pyridine-2-sulfonamide,
2) N-(2-(4-(6-fluorobenzo[d]thiazol-2-yl)piperazine-1-carbonyl)phenyl)-pyridine-2-sulfonamide,
3) N-(2-(4-(6-bromobenzo[d]thiazol-2-yl)piperazine-1-carbonyl)phenyl)-pyridine-2-sulfonamide,
4) N-(2-(4-(6-chlorobenzo[d]thiazol-2-yl)piperazine-1-carbonyl)phenyl)-pyridine-2-sulfonamide hydrochloride,
5) N-(2-(4-(4-methylbenzo[d]thiazol-2-yl)piperazine-1-carbonyl)phenyl)-pyridine-2-sulfonamide,
6) N-(2-(4-(7-chlorobenzo[d]thiazol-2-yl)piperazine-1-carbonyl)phenyl)-pyridine-2-sulfonamide,
7) N-(2-(4-(5-(trifluoromethyl)benzo[d]thiazol-2-yl)piperazine-1-carbonyl)phenyl)pyridine-2-sulfonamide,
8) N-(2-(4-(6-chlorobenzo[d]thiazol-2-yl)piperazine-1-carbonyl)phenyl)-5-(trifluoromethyl)pyridine-2-sulfonamide,
9) N-(2-(4-(6-bromobenzo[d]thiazol-2-yl)piperazine-1-carbonyl)phenyl)-6-methylpyridine-2-sulfonamide dihydrochloride,
10) N-(3-(4-(6-chlorobenzo[d]oxazol-2-yl)piperazine-1-carbonyl)-phenyl)-pyridine-2-sulfonamide,
11) N-(3-(4-(6-chlorobenzo[d]thiazol-2-yl)piperazine-1-carbonyl)-phenyl)-pyridine-2-sulfonamide,
12) N-(3-(4-(6-chlorobenzo[d]thiazol-2-yl)piperazine-1-carbonyl)-phenyl)-6-methylpyridine-2-sulfonamide,
13) N-(4-(4-(6-fluorobenzo[d]oxazol-2-yl)piperazine-1-carbonyl)-phenyl)-pyridine-2-sulfonamide,
14) N-(4-(4-(6-chlorobenzo[d]oxazol-2-yl)piperazine-1-carbonyl)-phenyl)-pyridine-2-sulfonamide,
15) N-(4-(4-(6-chlorobenzo[d]thiazol-2-yl)piperazine-1-carbonyl)-phenyl)-pyridine-2-sulfonamide,
16) N-(2-(4-(6-bromobenzo[d]thiazol-2-yl)piperazine-1-carbonyl)-phenyl)-quinoline-8-sulfonamide,
17) N-(2-(4-(6-chlorobenzo[d]oxazol-2-yl)piperazine-1-carbonyl)-phenyl)-quinoline-8-sulfonamide,
18) N-(2-(4-(6-chlorobenzo[d]thiazol-2-yl)piperazine-1-carbonyl)-phenyl)-quinoline-8-sulfonamide,
19) N-(2-(4-(6-(trifluoromethoxy)benzo[d]thiazol-2-yl)piperazine-1-carbonyl)-phenyl)quinoline-8-sulfonamide,
20) N-(2-(4-(4-methylbenzo[d]thiazol-2-yl)-1,4-diazepane-1-carbonyl)-phenyl)quinoline-8-sulfonamide,
21) N-(2-(1-(6-methylbenzo[d]oxazol-2-yl)piperidin-4-yloxy)phenyl)-pyridine-2-sulfonamide,
22) N-(2-(1-(6-chlorobenzo[d]oxazol-2-yl)piperidin-4-yloxy)phenyl)-pyridine-2-sulfonamide,
23) N-(2-(1-(5-tert-butylbenzo[d]oxazol-2-yl)piperidin-4-yloxy)phenyl)-pyridine-2-sulfonamide,
24) N-(2-(1-(5-chlorobenzo[d]oxazol-2-yl)piperidin-4-yloxy)phenyl)pyridine-2-sulfonamide,
25) N-(2-(1-(benzo[d]thiazol-2-yl)piperidin-4-yloxy)phenyl)pyridine-2-sulfonamide,
26) N-(2-(1-(6-chlorobenzo[d]thiazol-2-yl)piperidin-4-yloxy)phenyl-pyridine-2-sulfonamide,
27) N-(2-(1-(6-bromobenzo[d]thiazol-2-yl)piperidin-4-yloxy)phenyl)-pyridine-2-sulfonamide,
28) N-(2-((1-(benzo[d]thiazol-2-yl)pyrrolidin-3-yl)methoxy)phenyl)-pyridine-2-sulfonamide,
29) N-(2-((1-(6-fluorobenzo[d]thiazol-2-yl)pyrrolidin-3-yl)methoxy)phenyl)-pyridine-2-sulfonamide,
30) N-(2-((1-(6-chlorobenzo[d]thiazol-2-yl)pyrrolidin-3-yl)methoxy)phenyl)pyridine-2-sulfonamide,
31) N-(2-((1-(4-methylbenzo[d]thiazol-2-yl)pyrrolidin-3-yl)methoxy)phenyl)-pyridine-2-sulfonamide,
32) N-(2-((1-(4-methoxybenzo[d]thiazol-2-yl)pyrrolidin-3-yl)methoxy)phenyl)-pyridine-2-sulfonamide,
33) lithium N-(2-(4-(6-bromobenzo[d]thiazol-2-yl)piperazine-1-carbonyl)phenyl)-pyridine-2-sulfonamide,
34) sodium N-(2-(4-(6-bromobenzo[d]thiazol-2-yl)piperazine-1-carbonyl)phenyl)-pyridine-2-sulfonamide, and
35) potassium N-(2-(4-(6-bromobenzo[d]thiazol-2-yl)piperazine-1-carbonyl)phenyl)-pyridine-2-sulfonamide.

The purpose of the invention also concerns the pharmaceutically acceptable salts of the compounds of general formula I.

The present invention also concerns the compounds of general formula I as well as their pharmaceutically acceptable salts for their use as a medicine.

The present invention also concerns the compounds of general formula I as well as their pharmaceutically acceptable salts for their use as blockers of Kv potassium channels, and more particularly of the Kv1.5, Kv4.3 or Kv11.1 channels.

The invention also concerns the compounds of general formula I as well as their pharmaceutically acceptable salts for their use as medicine intended for the treatment and/or prevention of illnesses requiring blockers of Kv potassium channels, and more particularly channels Kv1.5, Kv4.3 and Kv11.1.

The invention also concerns the compounds of general formula I as well as their pharmaceutically acceptable salts for their use as medicine intended for the treatment and/or prevention of atrial fibrillation, heart rhythm disorders of the auricles and/or the ventricles, and pathologies in which the cell cycle and/or cell proliferation and/or regeneration are impaired (cancer, chronic inflammation).

"Impaired" is understood to mean a deterioration from an initial state.

The invention also extends to pharmaceutical compositions characterised in that they contain as their active principle a compound of general formula I or one of its pharmaceutically acceptable salts.

The invention also concerns a pharmaceutical composition characterised in that it contains a compound of general formula I or one of its pharmaceutically acceptable salts in association with at least one pharmaceutically acceptable excipient.

The pharmaceutical compositions according to the invention can be administered orally, sublingually, subcutaneously, intramuscularly, intravenously, transdermally, locally or rectally. In this case the active ingredient may be administered in the form of administration units, blended with traditional pharmaceutical supports, to animals or to human beings. The appropriate administration unit forms include orally administered forms such as pills, capsules, powders, granules and oral solutions or suspensions, sublingual and by-mouth forms of administration, the subcutaneous, topical, intramuscular, intravenous, intranasal or intraocular forms of administration, and the rectal forms of administration. The formulations appropriate for the chosen form of administration are known by the skilled man in the art and described, for example, in: Remington, The science and Practice of Pharmacy, 19$^{th}$ edition, 1995, Mack Publishing Company.

The dosages of the compounds of formula I in the compositions of the invention can be adjusted to obtain a quantity of active substance which is effective in obtaining the desired therapeutic response for a composition particular to the method of administration. The effective dose of a compound of the invention varies according to numerous parameters such as, for example, the chosen method of administration, weight, age, sex, the nature of the pathology and the sensitivity of the individual requiring treatment. Accordingly, the optimum posology must be determined in accordance with parameters judged relevant, by the specialist in the field.

The present invention also extends to the methods of chemical preparation of the compounds of general formula I as notably defined below.

Synthesis

The compounds of the present invention can be synthesised by using the methods of synthesis described below, or by using methods of synthesis known to the skilled man in the art.

Method 1 (when B=N)

This method of synthesis of the compounds of general formula I with B=N (diagram 1) is characterised by the following successive steps:

(a1) A derivative of general formula II for which R1, A and n are as defined in general formula I is condensed, with a derivative of isatoic anhydride XV for which R2 is as defined in general formula I, in the presence of a base such as DMAP, notably in a blend of solvents such as THF and DMF.

(a2) The intermediate III obtained is then condensed with a sulfonyl chloride of general formula IV for which HetAr is as defined in general formula I in the presence of a base such as pyridine, notably in a solvent such as dichloromethane.

(a3) The compound of formula I obtained in the previous step (a2) may be salified in the presence of a pharmaceutically acceptable base or acid in order to give a pharmaceutically acceptable salt of the compound of formula I.

Diagram 1:

Method 2 (when B=N)

This method of synthesis of the compounds of general formula I with B=N (diagram 2) is characterised by the following successive steps:

(b1) A derivative of general formula V for which R3 represents a linear or branched $C_1$-$C_4$ alkyl such as a methyl or ethyl and R2 is such as defined in general formula I is condensed, with a sulfonyl chloride of general formula IV for which HetAr is as defined in general formula I.

in the presence of a base such as pyridine, notably in a solvent such as dichloromethane.

(b2) The compound VI obtained in this manner is saponified, notably in the presence of a base such as potash, in particular in a solvent such as ethanol, to give the compound VII.

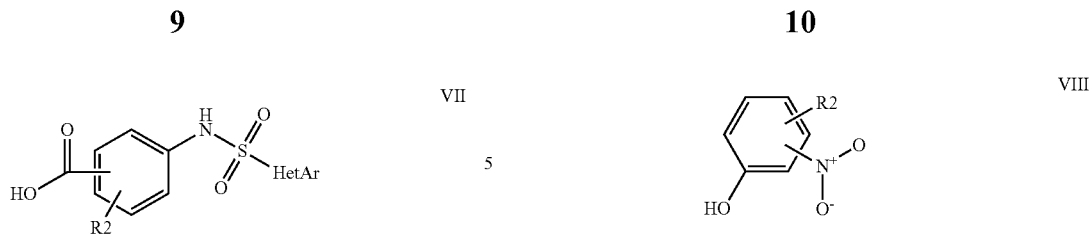

(b3) The latter is coupled with the previously defined intermediate II to give the compound of formula I, notably under process conditions such as in the presence of TBTU and Et$_3$N in a solvent such as acetonitrile.

(b4) The compound of formula I obtained in the previous step (b3) may be converted into a salt in the presence of a pharmaceutically acceptable base or acid in order to give a pharmaceutically acceptable salt of the compound of formula I.

Diagram 2:

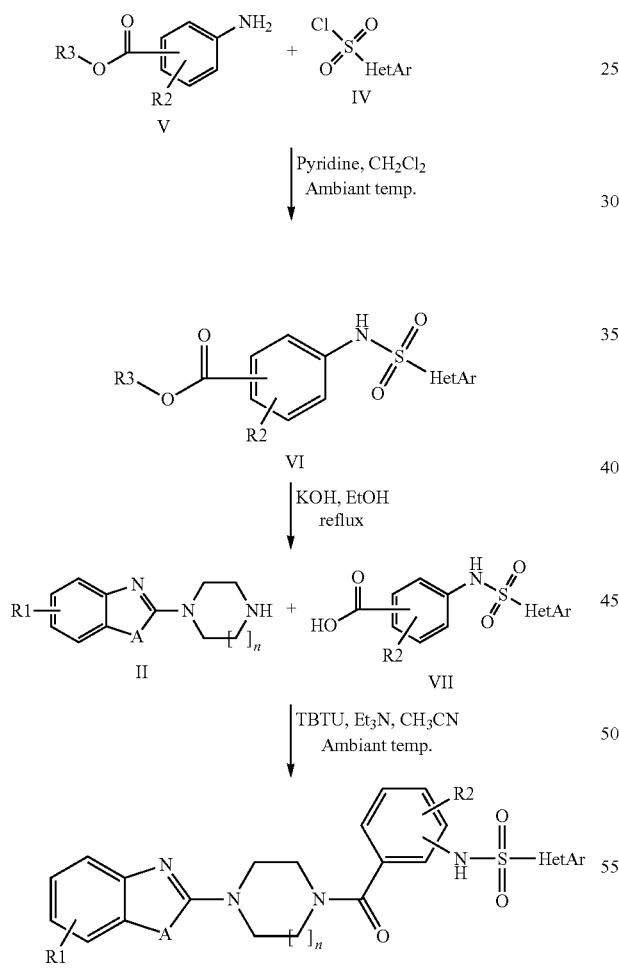

Method 3 (when B=CH)

This method of synthesis of the compounds of general formula I with B=CH (diagram 3) is characterised by the following successive steps:

(c1) A derivative of general formula VIII for which R2 is as defined in general formula I is condensed,

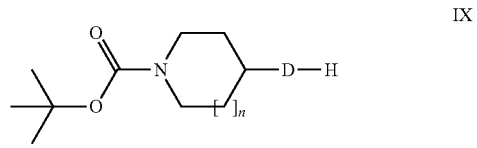

with a derivative of general formula IX for which D and n are as defined in general formula I when B represents CH.

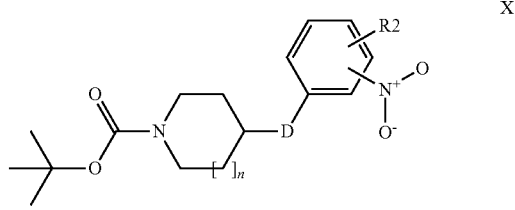

notably under process conditions such as those of Mitsunobu coupling in the presence of triphenylphosphine, of diethylazodicarboxylate in THF.

(c2) The intermediate X obtained in this manner

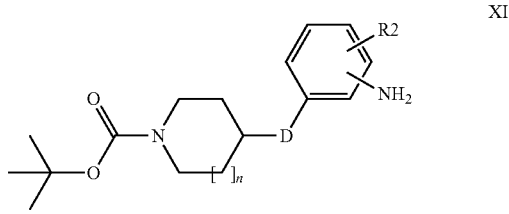

is then reduced, notably by using process conditions such as palladium on carbon in an atmosphere of hydrogen in a solvent such as ethanol, which enables intermediate XI to be isolated.

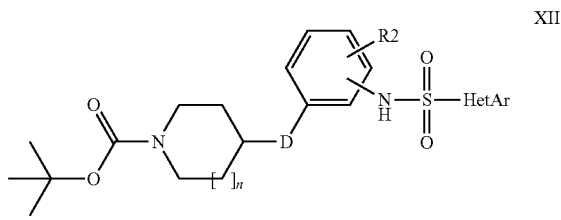

(c3) The latter is coupled with a sulfonyl chloride of general formula IV for which HetAr is as defined in general formula I, in the presence of a base such as pyridine, notably in a solvent such as dichloromethane, leading to intermediate XII.

(c4) The amide group of the latter is hydrolysed, notably in the presence of trifluoroacetic acid, notably in a solvent such as dichloromethane to give intermediate XIII.

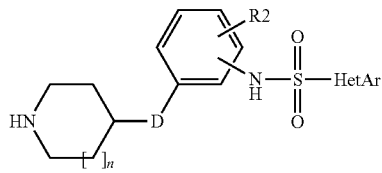

XIII (c5) The compound XIII is then coupled with intermediate XIV for which R1 and A are as defined in general formula I,

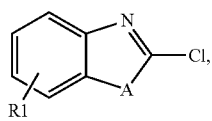

XIV notably under process conditions such as in the presence of bicarbonate of soda in a blend of solvents such as ethanol and water, to give the compound of general formula I.

(c6) The compound of formula I obtained in the previous step (c5) may be salified in the presence of a pharmaceutically acceptable base or acid in order to give a pharmaceutically acceptable salt of the compound of formula I.

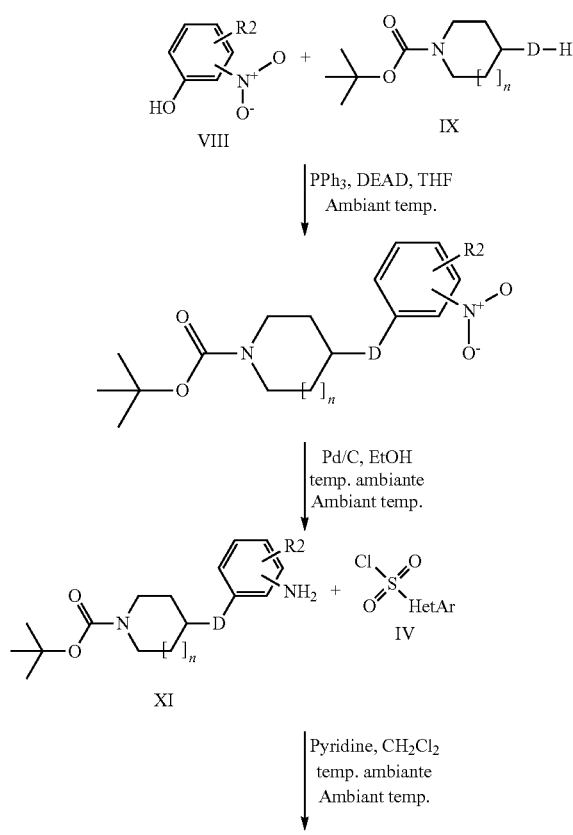

The intermediate and final compounds may if desired be purified using one or more methods of purification chosen from among extraction, filtration, chromatography on silica gel, preparatory HPLC in the normal or reverse phase, or crystallisation.

The starting materials used in the methods described above are commercial or easily accessible to the skilled man in the art using methods described in the literature.

The following examples illustrate the invention without limiting its scope.

The elementary analyses and the mass spectra and NMR confirm the structures of the compounds.

EXAMPLES

A) Intermediates

Intermediates 1:

a) 6-Fluoro-benzooxazole-2-thiol (1a)

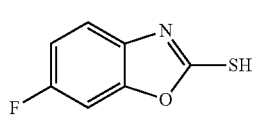 [SMILES: Fc1ccc2nc(S)oc2c1]

2-amino-5-fluoro-phenol (10 g, 79 mmol) is placed in the presence of potassium O-ethylcarbonodithioate (27.7 g, 173 mmol) in 100 mL of ethanol at reflux overnight. After reduction to dryness the residue is triturated in a solution of HCl 1N, filtered and then rinsed with HCl 1N. After drying under vacuum, 13.8 g of a brown solid is isolated (quantitative yield).

b) 5-tert-Butyl-benzooxazole-2-thiol (1b)

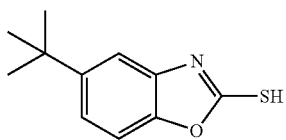

Intermediate 1b (solid) is prepared from 2-amino-4-tert-butyl-phenol using the procedure described for intermediate 1a (yield 94%). TLC silica gel 60 F 254 Merck, $CH_2Cl_2$-MeOH:90-10, Rf=0.83.

c) 7-Chloro-benzothiazole-2-thiol (1c)

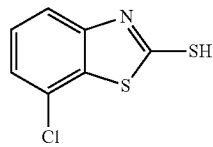 [SMILES: Sc1nc2cccc(Cl)c2s1]

Intermediate 1c (solid) is prepared from 3-chloro-2-fluoro-phenylamine using the procedure described for intermediate 1a using DMF at reflux (quantitative yield). TLC silica gel 60 F 254 Merck, $CH_2O_2$-MeOH:95-5, Rf=0.70.

d) 5-Trifluoromethyl-benzothiazole-2-thiol (1d)

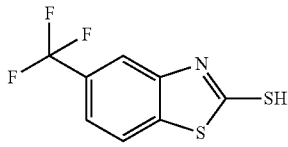

Intermediate 1d (solid) is prepared from 2-bromo-5-trifluoromethyl-phenylamine using DMF as solvent using the procedure described for intermediate 1a (yield 28%). TLC silica gel 60 F 254 Merck, $CH_2Cl_2$-MeOH:95-5, Rf=0.73.

e) 6-Bromo-benzothiazole-2-thiol (1e)

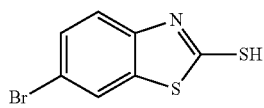

Intermediate 1e (solid) is prepared from 4-bromo-2-fluoro-phenylamine using the procedure described for intermediate 1a (quantitative yield). TLC silica gel 60 F 254 Merck, $CH_2Cl_2$-MeOH:95-5, Rf=0.75.

f) 6-Methyl-benzooxazole-2-thiol (1f)

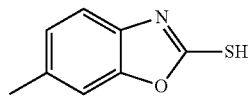

8 g (65 mmol) of 2-amino-5-methyl-phenol is placed in the presence of potash (4.37 g, 78 mmol) in a mixture of 100 mL of $CS_2$ and 150 mL of EtOH and heated at 100° C. for 8 h. After reduction to dryness the medium is taken up in the water and extracted using AcOEt and after drying the organic phases are reduced to dryness. The residue is taken up by $Et_2O$ and the crystals obtained are filtered and then rinsed in petroleum ether. 10 g of beige crystals is isolated (yield: 94%). TLC silica gel 60 F 254 Merck, $CH_2Cl_2$-MeOH:95-5, Rf=0.75.

g) 5-Chloro-benzooxazole-2-thiol (1g)

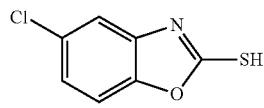

Intermediate 1b (solid) is prepared from 2-amino-4-chloro-phenol using the procedure described for intermediate 1f (yield: 46%). TLC silica gel 60 F 254 Merck, Petroleum ether-AcOEt:50-50, Rf=0.70.

Intermediates 2:

a) 2-Chloro-6-fluoro-benzothiazole (2a)

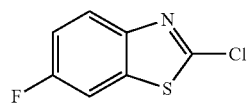 [SMILES: Fc1ccc2nc(Cl)sc2c1]

0.5 g (2.97 mmol) of 6-fluoro-benzothiazol-2-ylamine is placed in the presence of isoamyl nitrite (0.52 g, 4.46 mmol) and $CuCl_2.2H_2O$ (0.61 g, 0.57 mmol) in 10 mL of acetonitrile. The reaction medium is heated to 65° C. for 3 h and then reduced to dryness; the residue is taken up by water and extracted using ethyl acetate. The organic phases are dried and then evaporated, and the residue obtained is purified by flash chromatography on silica ($CH_2Cl_2$—AcOEt, gradient b) 2-Chloro-4-methyl-benzothiazole (2b)

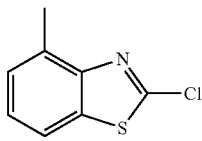

Intermediate 2b (solid) is prepared from 4-methyl-benzothiazol-2-ylamine using the procedure described for intermediate 2a (yield: 89%). TLC silica gel 60 F 254 Merck, $CH_2Cl_2$-MeOH:95-5, Rf=0.83.

c) 2-Chloro-4-methoxy-benzothiazole (2c)

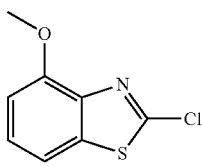

Intermediate 2c (solid) is prepared from 4-methoxy-benzothiazol-2-ylamine using the procedure described for intermediate 2a (yield: 47%). TLC silica gel 60 F 254 Merck, Petroleum ether-AcOEt:70-30, Rf=0.77.

d) 6-Bromo-2-chloro-benzothiazole (2d)

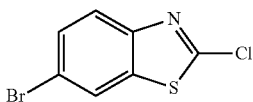 [SMILES: Clc1nc2ccc(Br)cc2s1]

Intermediate 2c (solid) is prepared from 6-bromo-benzothiazol-2-ylamine using the procedure described for intermediate 2a (yield: 75%). TLC silica gel 60 F 254 Merck, $CH_2Cl_2$-MeOH:95-5, Rf=0.83.

e) 2-Chloro-6-methyl-benzooxazole (2e)

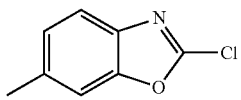

Intermediate 1f is placed at 0° C. in 1.76 mL of thionyl chloride. 0.47 mL of DMF is poured drop-by-drop in such a way as to keep the reaction medium at 0° C., after which it is stirred for 1 h at this temperature. After evaporation under vacuum the medium is taken up by water and extracted using ethyl acetate. The organic phases are dried and reduced to dryness. The residue obtained is purified by flash chromatography on silica (Petroleum ether-AcOEt, gradient 100-0 to 80-20 over 20 min). 0.66 g of oil is obtained (yield 65%). TLC silica gel 60 F 254 Merck, $CH_2Cl_2$-MeOH:90-10, Rf=0.80.

f) 2,6-Dichloro-benzooxazole (2f)

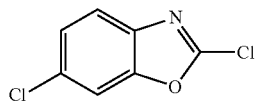 [SMILES: Clc1ccc2nc(Cl)oc2c1]

Intermediate 2f (solid) is prepared from 6-chloro-benzooxazole-2-thiol using the procedure described for intermediate 2e (yield: 42%). TLC silica gel 60 F 254 Merck, AcOEt, Rf=0.87.

g) 5-tert-Butyl-2-chloro-benzooxazole (2q)

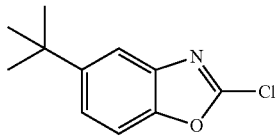

Intermediate 2g (oil) is prepared from intermediate 1b using the procedure described for intermediate 2e (yield: 42%). TLC silica gel 60 F 254 Merck, Petroleum ether-AcOEt:50-50, Rf=0.76.

h) 2,5-Dichloro-benzooxazole (2h)

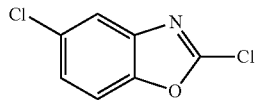 [SMILES: Clc1ccc2oc(Cl)nc2c1]

Intermediate 2h (solid) is prepared from intermediate 1g using the procedure described for intermediate 2e (yield: quantitative). TLC silica gel 60 F 254 Merck, Petroleum ether-AcOEt:50-50, Rf=0.68.

i) 2-bromo-6-(trifluoromethoxy)benzo[d]thiazole (2i)

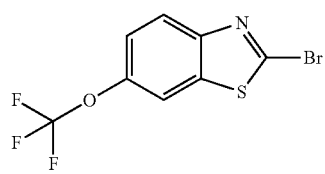 [SMILES: FC(F)(F)Oc1ccc2nc(Br)sc2c1]

Intermediate 2i (solid) is prepared from 2-amino-6-(trifluoromethoxy)benzothiazole using the procedure described for intermediate 2a using $CuBr_2$ (yield: 90%). TLC silica gel 60 F 254 Merck, $CH_2Cl_2$MeOH:95-5, Rf=0.93.

Intermediates 3:

a) 6-Fluoro-2-piperazin-1-yl-benzooxazole (3a)

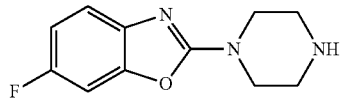 [SMILES: Fc1ccc2nc(N3CCNCC3)oc2c1]

intermediate 1a (9 g, 53.2 mmol) is placed in the presence of piperazine (22.91 g, 266 mmol) in 45 mL of butanol at 180° C. for 40 min under microwaves. After reduction to dryness the medium is taken up by water and extracted using ethyl acetate. The organic phases are dried and then evaporated, and the residue obtained is purified by flash chromatography on silica ($CH_2Cl_2$-MeOH, gradient 98-2 to 80-20 over 20 min). 2.73 g of brown oil is obtained (yield 23%). TLC silica gel 60 F 254 Merck, $CH_2Cl_2$-MeOH:90-10, Rf=0.11.

b) 6-Chloro-2-piperazin-1-yl-benzooxazole (3b)

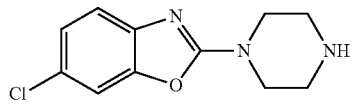 [SMILES: Clc1ccc2nc(N3CCNCC3)oc2c1]

Intermediate 3b (oil) is prepared from 6-chloro-2-benzoxazole-2-thiol using the procedure described for intermediate 3a (yield: 92%). TLC silica gel 60 F 254 Merck, $CH_2Cl_2$-MeOH:90-10, Rf=0.11.

c) 7-Chloro-2-piperazin-1-yl-benzothiazole (3c)

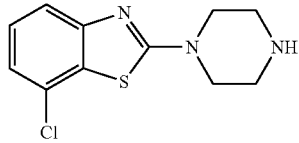 [SMILES: Clc1cccc2nc(N3CCNCC3)sc12]

Intermediate 3c (solid) is prepared from intermediate 1c using the procedure described for intermediate 3a (yield: 79%). TLC silica gel 60 F 254 Merck, $CH_2Cl_2$-MeOH:90-10, Rf=0.15.

d) 2-Piperazin-1-yl-5-trifluoromethyl-benzothiazole (3d)

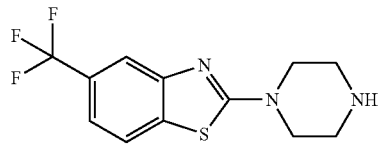 [SMILES: FC(F)(F)c1ccc2sc(N3CCNCC3)nc2c1]

Intermediate 3d (solid) is prepared from intermediate 1d using the procedure described for intermediate 3a (yield: 91%). TLC silica gel 60 F 254 Merck, $CH_2Cl_2$-MeOH:95-5, Rf=0.20.

e) 6-Fluoro-2-piperazin-1-yl-benzothiazole (3e)

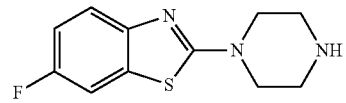 [SMILES: Fc1ccc2nc(N3CCNCC3)sc2c1]

Piperazine (0.33 g, 3.84 mmol) is placed in 6 mL of ethanol, the sodium bicarbonate (0.56 g, 6.72 mmol) diluted in 8 mL of water is added, and then 0.36 g (1.92 mmol) of intermediate 2a diluted in 8 mL of ethanol is poured drop-by-drop. The reaction medium is heated to reflux overnight and then reduced to dryness. After extraction using ethyl acetate the organic phases are evaporated and the residue obtained is purified by flash chromatography on silica ($CH_2Cl_2$-MeOH, gradient 100-0 to 90-10 over 45 min). 0.39 g of solid is obtained (yield 86%). TLC silica gel 60 F 254 Merck, $CH_2Cl_2$-MeOH:95-5, Rf=0.05.

f) 6-Bromo-2-piperazin-1-yl-benzothiazole (3f)

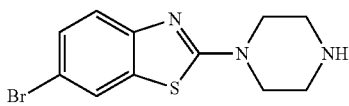

Intermediate 3f (solid) is prepared from intermediate 2d using the procedure described for intermediate 3e (yield: 92%). TLC silica gel 60 F 254 Merck, $CH_2Cl_2$-MeOH:95-5, Rf=0.14.

g) 6-Chloro-2-piperazin-1-yl-benzothiazole (3g)

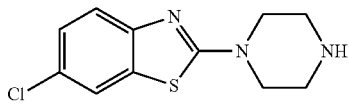 [SMILES: Clc1ccc2nc(N3CCNCC3)sc2c1]

Intermediate 3g (solid) is prepared from 2,6-dichloro-1,3-benzothiazole using the procedure described for intermediate 3e (yield: 84%). TLC silica gel 60 F 254 Merck, $CH_2Cl_2$-MeOH:90-10, Rf=0.23.

h) 4-Methyl-2-piperazin-1-yl-benzothiazole (3h)

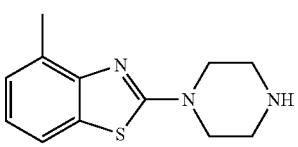 [SMILES: Cc1cccc2sc(N3CCNCC3)nc12]

Intermediate 3h (solid) is prepared from intermediate 2b using the procedure described for intermediate 3e (yield: 79%). TLC silica gel 60 F 254 Merck, $CH_2Cl_2$—AcOEt:95-5, Rf=0.05.

i) 2-(Piperazin-1-yl)-6-(trifluoromethoxy)benzothiazole (3i)

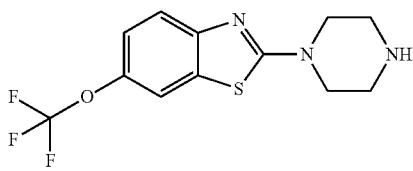 [SMILES: FC(F)(F)Oc1ccc2nc(N3CCNCC3)sc2c1]

Intermediate 3i (solid) is prepared from intermediate 2i using the procedure described for intermediate 3e (yield: 88%). TLC silica gel 60 F 254 Merck, $CH_2Cl_2$-MeOH:95-5, Rf=0.22.

j) 2-[1,4]Diazepan-1-yl-4-methyl-benzothiazole (3j)

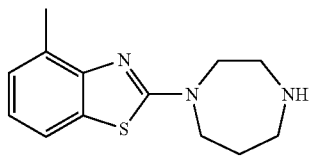 [SMILES: Cc1cccc2sc(N3CCCNCC3)nc12]

Intermediate 3j (oil) is prepared from intermediate 2b and [1,4]diazepane using the procedure described for intermediate 3e (yield: 83%). TLC silica gel 60 F 254 Merck, $CH_2Cl_2$-MeOH:95-5, Rf=0.10.

Intermediates 4:

a) 5-Trifluoromethyl-pyridine-2-sulfonyl chloride (4a)

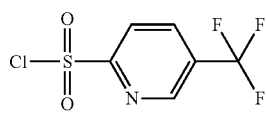

0.8 g (4.47 mmol) of 5-trifluoromethyl-pyridine-2-thiol is placed at −8° C. in 16 mL of $H_2SO_4$. 16.96 mL (35.7 mmol) of a 13% sodium hypochlorite solution is poured gently such that the temperature of the reaction medium does not exceed 5° C. This mixture is then stirred for 45 min, taken up by water and then extracted using AcOEt. After drying followed by reduction to dryness of the organic phases, an oil is isolated (yield: 79%) and used as such for the next reactions.

b) Pyridine-2-sulfonyl chloride (4b)

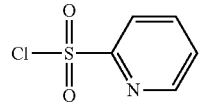

Intermediate 4b (oil) is prepared from pyridine-2-thiol using the procedure described for 4a (yield: 96%).

c) 6-methylpyridine-2-sulfonyl chloride (4c)

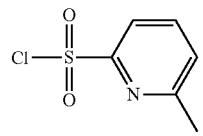

Intermediate 4c (oil) is prepared from 6-methylpyridine-2-thiol using the procedure described for 4a (yield: 96%).

Intermediates 5:

a) 3-(pyridine-2-sulfonamido)benzoic acid (5a)

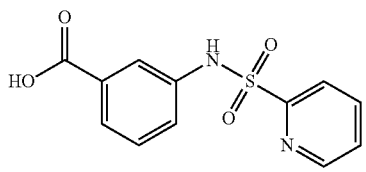 [SMILES: O=C(O)c1cccc(NS(=O)(=O)c2ccccn2)c1]

0.68 g (4.13 mmol) of ethyl 3-aminobenzoate is placed in 10 mL of $CH_2Cl_2$ in the presence of 0.4 mL of pyridine and a solution of intermediate 4b diluted in 3 mL of $CH_2Cl_2$ is poured drop-by-drop. The reaction medium is stirred for 8 h and then reduced to dryness. The residue is taken up in water and then extracted using AcOEt. After drying followed by reduction to dryness of the organic phases, a solid is isolated and then purified by flash chromatography on silica ($CH_2Cl_2$—AcOEt, gradient 100-0 to 90-10 over 45 min). 1.14 g of white solid is obtained (yield: 90%). TLC silica gel 60 F 254 Merck, $CH_2Cl_2$—AcOEt:90-10, Rf=0.26. This solid (3.72 mmol) is placed in 17 mL of EtOH in the presence of 0.41 g (7.44 mmol) of soda and the mixture is heated to reflux for 9h30. After reduction to dryness the medium is taken up by water and extracted using AcOEt. The aqueous phase is then acidified (pH=1) with HCl 1N and then extracted using AcOEt. After drying followed by reduction to dryness of the organic phases, a solid is obtained. It is triturated in petroleum b) 3-(6-Methyl-pyridine-2-sulfonylamino)-benzoic acid (5b)

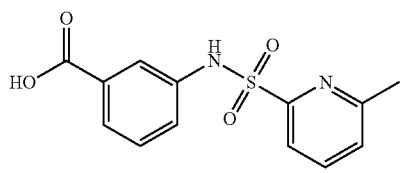 [SMILES: Cc1cccc(S(=O)(=O)Nc2cccc(C(=O)O)c2)n1]

Intermediate 5b (solid) is prepared using intermediate 4c and ethyl 3-aminobenzoate using the procedure described for 5a.
(yield: 94%).
TLC silica gel 60 F 254 Merck, CH$_2$Cl$_2$-MeOH:85-15, Rf=0.36.

c) 4-(Pyridine-2-sulfonylamino)-benzoic acid (5c)

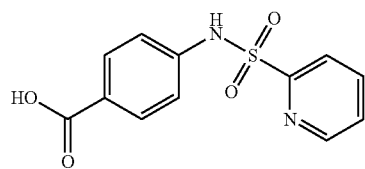 [SMILES: O=C(O)c1ccc(NS(=O)(=O)c2ccccn2)cc1]

Intermediate 5c (solid) is prepared using intermediate 4b and ethyl 4-aminobenzoate using the procedure described for 5a.
(yield: 50%).
TLC silica gel 60 F 254 Merck, CH$_2$Cl$_2$-MeOH:85-15, Rf=0.37.

Intermediates 6:

a) N-(2-(piperidin-4-yloxy)phenyl)pyridine-2-sulfonamide trifluoroacetate (6a)

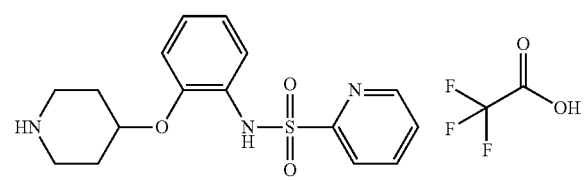

10 g (49.7 mmol) of tert-butyl 4-hydroxypiperidine-1-carboxylate is placed in the presence of 6.91 g (49.7 mmol) of 2-nitrophenol and 16.94 g (64.6 mmol) of PPh$_3$. 11.25 g (64.6 mmol) of DEAD is added to this mixture per fraction and the reaction medium is stirred for 2 h at ambient temperature and then reduced to dryness. The residue is taken up in water and extracted using AcOEt. After drying followed by evaporation of the organic phases the residue obtained is purified by flash chromatography on silica (Petroleum ether-AcOEt, gradient 80-20 to 60-40 over 20 min). The yellow oil obtained crystallises after trituration in a mixture of petroleum ether-Et$_2$O and 13.2 g of solid is isolated (yield 82%). TLC silica gel 60 F 254 Merck, Petroleum ether-AcOEt:50-50, Rf=0.40.

The solid previously obtained (41.9 mmol) is placed in a stainless steel reactor in the presence of 223 mg of Pd on carbon in 100 mL of MeOH under 5 bars of hydrogen and stirred for 2 h at ambient temperature. After filtration on celite followed by evaporation, 12.4 g of an orange oil is isolated (quantitative yield). TLC silica gel 60 F 254 Merck, Petroleum ether-AcOEt:80-20, Rf=0.44.

4.5 g (15.39 mmol) of previously isolated oil is placed in 200 mL of CH$_2$Cl$_2$ in the presence of intermediate 4b and of pyridine (1.46 g, 18.47 mmol) and stirred at ambient temperature for 3 h. The reaction medium is taken up by water and then extracted using AcOEt. After drying followed by evaporation of the organic phases the residue obtained is purified by flash chromatography on silica (Petroleum ether-AcOEt, gradient 70-30 to 50-50 over 30 min). 5.5 g of brown solid is isolated (yield: 82%). TLC silica gel 60 F 254 Merck, Petroleum ether-AcOEt:50-50, Rf=0.50.

The solid previously obtained (12.7 mmol) is placed in the presence of 14.7 g (127 mmol) of trifluoroacetic acid in 40 mL of CH$_2$Cl$_2$ and stirred for 2 h at ambient temperature. After evaporation under reduced pressure the residue is triturated in a mixture of Et$_2$O/acetone and 5.34 g of intermediate 6a (a beige solid) is isolated by filtration (yield 94%). TLC silica gel 60 F 254 Merck, Petroleum ether-AcOEt:50-50, Rf=0.36.

b) N-(2-(pyrrolidin-3-ylmethoxy)phenyl)pyridine-2-sulfonamide trifluoroacetate (6b)

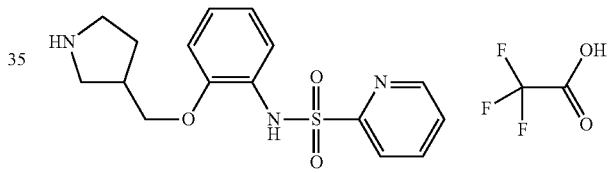

Intermediate 6b (solid) is prepared using tert-butyl 3-(hydroxymethyl)pyrrolidine-1-carboxylate instead of tert-butyl 4-hydroxypiperidine-1-carboxylate using the procedure described for 6a (yield: 39% over the 4 steps).
TLC silica gel 60 F 254 Merck, CH$_2$Cl$_2$-MeOH:90-10, Rf=0.25.

B) Compounds According to the Invention

Example 1

N-(2-(4-(6-fluorobenzo[d]oxazol-2-yl)piperazine-1-carbonyl)phenyl)-5-(trifluoromethyl)pyridine-2-sulfonamide (1)

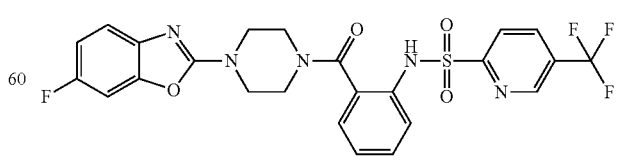

Compound 1 is prepared using synthesis method 1: intermediate 3a (2.5 g, 11.30 mmol) is placed in the presence of 1H-benzo[d][1,3]oxazine-2,4-dione (1.83 g, 11.3 mmol) and of DMAP (138 mg, 1.13 mmol) in 25 mL of THF and 5 mL of DMF and the mixture is stirred overnight at ambient temperature. After reduction to dryness the residue is taken up in water and extracted using AcOEt. After the organic phases are dried and after reduction to dryness the residue obtained is purified by flash chromatography on silica (CH$_2$Cl$_2$-MeOH, gradient 100-0 to 95-5 over 40 min). 0.47 g of solid is obtained (yield: 32%). It is then placed in 3 mL of dichloromethane in the presence of 0.119 g (0.48 mmol) of intermediate 4a and 39 µL of pyridine. The mixture is then stirred overnight at ambient temperature and then taken up by water and extracted using dichloromethane. After the organic phases are dried and after reduction to dryness the residue obtained is purified by flash chromatography (CH$_2$Cl$_2$-MeOH, gradient 100-0 to 95-5 over 65 min). 90 mg of solid is obtained (yield: 35%).

TLC silica gel 60 F 254 Merck, CH$_2$Cl$_2$-MeOH: 95-5, Rf=0.48.

NMR $^1$H (CDCl$_3$) ppm: 8.94 (s, 1H), 8.69 (s, 1H), 8.19 (m, 2H), 7.74 (d, 1H), 7.41 (t, 1H), 7.26 (m, 2H), 7.17 (t, 1H), 7.07 (d, 1H), 6.95 (t, 1H), 3.76 (m, 8H).

MS (-ESI) m/z 548 (M-H-)

Example 2

N-(2-(4-(6-fluorobenzo[d]thiazol-2-yl)piperazine-1-carbonyl)phenyl)-pyridine-2-sulfonamide (2)

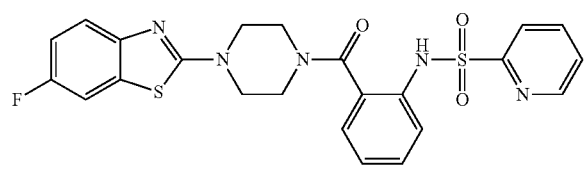 [SMILES: O=C(c1ccccc1NS(=O)(=O)c1ccccn1)N1CCN(c2nc3ccc(F)cc3s2)CC1]

Compound 2 is prepared using synthesis method 1 using intermediate 3e for the first step (yield: 87%) and intermediate 4b for the second step (yield: 30%).

TLC silica gel 60 F 254 Merck, CH$_2$Cl$_2$-MeOH: 95-5, Rf=0.58.

NMR $^1$H (CDCl$_3$) ppm: 8.65 (d, 1H), 8.58 (s, 1H), 8.03 (d, 1H), 7.89 (t, 1H), 7.77 (d, 1H), 7.50 (m, 1H), 7.39 (m, 3H), 7.12 (m, 3H), 3.62 (m, 8H).

MS (+ESI) m/z 498 (MH+)

Example 3

N-(2-(4-(6-bromobenzo[d]thiazol-2-yl)piperazine-1-carbonyl)phenyl)-pyridine-2-sulfonamide (3)

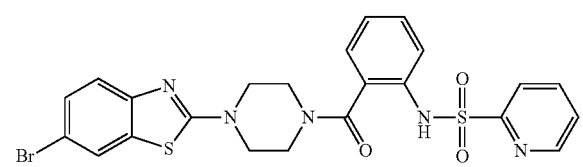 [SMILES: O=C(c1ccccc1NS(=O)(=O)c1ccccn1)N1CCN(c2nc3ccc(Br)cc3s2)CC1]

Compound 3 is prepared using synthesis method 1 using intermediate 3f for the first step (quantitative yield) and intermediate 4b for the second step (yield: 80%).

TLC silica gel 60 F 254 Merck, CH$_2$Cl$_2$-MeOH: 95-5, Rf=0.60.

mp=102° C.

NMR $^1$H (CDCl$_3$) ppm: 8.66 (d, 1H), 8.56 (s, 1H), 8.03 (d, 1H), 7.88 (t, 1H), 7.75 (m, 2H), 7.41 (m, 4H), 7.16 (m, 2H), 3.64 (m, 8H).

MS (+ESI) m/z 558 (MH+)

Example 4

N-(2-(4-(6-chlorobenzo[d]thiazol-2-yl)piperazine-1-carbonyl)phenyl)pyridine-2-sulfonamide hydrochloride (4)

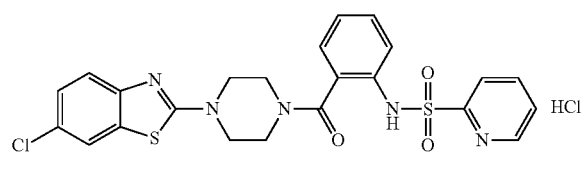 [SMILES: O=C(c1ccccc1NS(=O)(=O)c1ccccn1)N1CCN(c2nc3ccc(Cl)cc3s2)CC1 ; Cl]

Compound 4 is prepared using synthesis method 1 using intermediate 3g for the first step (yield: 72%) and intermediate 4b for the second step (yield: 27%) and then salified in the form of hydrochloride.

NMR $^1$H (DMSO) ppm: 10.70 (s, 1H), 8.7 (d, 1H), 8.0 (m, 1H), 7.8 (m, 2H), 7.6 (m, 1H), 7.4 (d, 1H), 7.3 (m, 3H), 7.2 (m, 1H), 7.1 (d, 1H), 3.6 (m, 8H).

MS (+ESI) m/z 514 (MH+ base)

Example 5

N-(2-(4-(4-methylbenzo[d]thiazol-2-yl)piperazine-1-carbonyl)phenyl)-pyridine-2-sulfonamide (5)

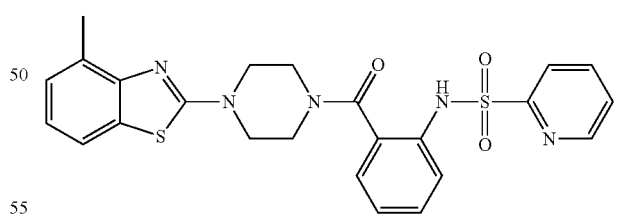

Compound 5 is prepared using synthesis method 1 using intermediate 3h for the first step (yield: 87%) and intermediate 4b for the second step (yield: 23%).

TLC silica gel 60 F 254 Merck, CH$_2$Cl$_2$-MeOH: 95-5, Rf=0.70.

NMR $^1$H (CDCl$_3$) ppm: 8.65 (m, 2H), 8.03 (d, 1H), 7.87 (t, 1H), 7.79 (d, 1H), 7.48 (d, 1H), 7.41 (m, 2H), 7.20 (d, 1H), 7.14 (m, 2H), 7.04 (t, 1H), 3.63 (m, 8H), 2.56 (s, 3H).

MS (+ESI) m/z 494 (MH+)

Example 6

N-(2-(4-(7-chlorobenzo[d]thiazol-2-yl)piperazine-1-carbonyl)phenyl)-pyridine-2-sulfonamide (6)

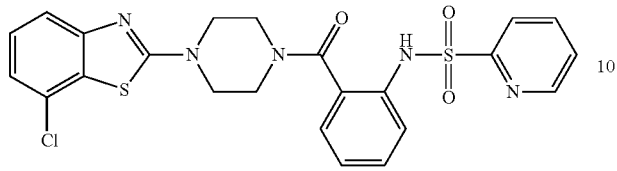

Compound 6 is prepared using synthesis method 1 using intermediate 3c for the first step (quantitative yield) and intermediate 4b for the second step (yield: 24%).

TLC silica gel 60 F 254 Merck, $CH_2Cl_2$-MeOH: 95-5, Rf=0.54.

NMR $^1$H (CDCl$_3$) ppm: 8.66 (d, 1H), 8.57 (s, 1H), 8.04 (d, 1H), 7.89 (t, 1H), 7.77 (d, 1H), 7.42 (m, 3H), 7.29 (m, 1H), 7.16 (m, 3H), 3.66 (m, 8H).

MS (+ESI) m/z 514 (MH+)

Example 7

N-(2-(4-(5-(trifluoromethyl)benzo[d]thiazol-2-yl)piperazine-1-carbonyl)phenyl)pyridine-2-sulfonamide (7)

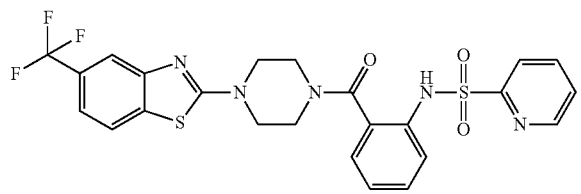 [SMILES: O=C(c1ccccc1NS(=O)(=O)c1ccccn1)N1CCN(c2nc3cc(C(F)(F)F)ccc3s2)CC1]

Compound 7 is prepared using synthesis method 1 using intermediate 3d for the first step (yield: 74%) and intermediate 4b for the second step (yield: 31%).

TLC silica gel 60 F 254 Merck, $CH_2Cl_2$-MeOH: 95-5, Rf=0.66.

NMR $^1$H (CDCl$_3$) ppm: 8.67 (d, 1H), 8.55 (s, 1H), 8.04 (d, 1H), 7.89 (t, 1H), 7.76 (s, 1H), 7.74 (dd, 2H), 7.41 (m, 3H), 7.21 (d, 1H), 7.14 (t, 1H), 3.68 (m, 8H).

MS (+ESI) m/z 548 (MH+)

Example 8

N-(2-(4-(6-chlorobenzo[d]thiazol-2-yl)piperazine-1-carbonyl)phenyl)-5-(trifluoromethyl)pyridine-2-sulfonamide (8)

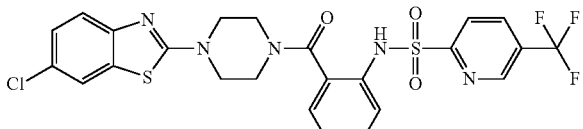

Compound 8 is prepared using synthesis method 1 using intermediate 3g for the first step (yield: 94%) and intermediate 4a for the second step (yield: 56%).

TLC silica gel 60 F 254 Merck, $CH_2Cl_2$-MeOH: 95-5, Rf=0.50.

NMR $^1$H (CDCl$_3$) ppm: 8.93 (s, 1H), 8.71 (s, 1H), 8.18 (m, 2H), 7.74 (d, 1H), 7.60 (s, 1H), 7.47 (d, 1H), 7.40 (t, 1H), 7.26 (m, 2H), 7.16 (t, 1H), 3.69 (m, 8H).

MS (−ESI) m/z 580 (M-H−)

Example 9

N-(2-(4-(6-bromobenzo[d]thiazol-2-yl)piperazine-1-carbonyl)phenyl)-6-methylpyridine-2-sulfonamide dihydrochloride (9)

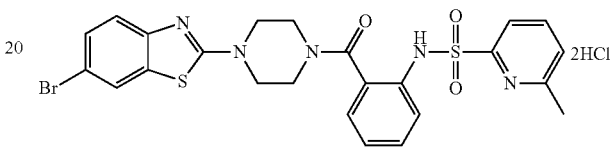

Compound 9 is prepared using synthesis method 1 using intermediate 3f for the first step (quantitative yield) and intermediate 4c for the second step (yield: 40%). The dihydrochloride is obtained by salt formation using a 5N solution of HCl in isopropanol (3 equivalents).

TLC silica gel 60 F 254 Merck, $CH_2Cl_2$-MeOH: 95-5, Rf=0.73.

mp=180° C.

NMR $^1$H (DMSO-d6) ppm: 10.03 (s, 1H), 8.07 (s, 1H), 7.93 (t, 1H), 7.70 (d, 1H), 7.53 (d, 1H), 7.42 (m, 2H), 7.33 (m, 2H), 7.21 (m, 2H), 3.68 (m, 8H), 2.55 (s, 3H).

MS (+ESI) m/z 572 (MH+)

Example 10

N-(3-(4-(6-chlorobenzo[d]oxazol-2-yl)piperazine-1-carbonyl)-phenyl)pyridine-2-sulfonamide (10)

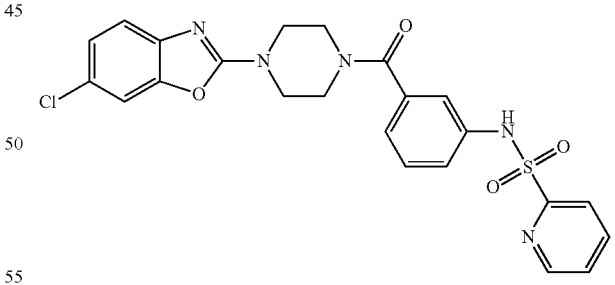

Compound 10 is prepared using synthesis method 2: intermediate 3b (0.16 g, 0.67 mmol) is placed in 21 mL of acetonitrile in the presence of 0.18 g (0.67 mmol) of intermediate 5a and 103 μL of Et$_3$N. 0.21 g (0.67 mmol) of TBTU is then added and the mixture is then stirred for 5 h at ambient temperature. After evaporation under reduced pressure the residue is taken up by water and extracted using AcOEt. After the organic phases are dried and after reduction to dryness the residue obtained is purified by flash chromatography (CH$_2$Cl$_2$-MeOH, gradient 99-1 to 95-5 over 65 min). 0.23 g of solid is obtained (yield: 68%).

Example 11

N-(3-(4-(6-chlorobenzo[d]thiazol-2-yl)piperazine-1-carbonyl)phenyl)-pyridine-2-sulfonamide (11)

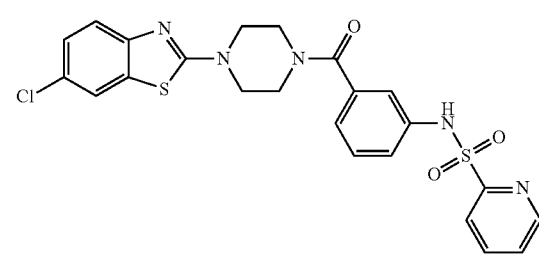 [SMILES: O=C(c1cccc(NS(=O)(=O)c2ccccn2)c1)N1CCN(c2nc3ccc(Cl)cc3s2)CC1]

Compound 11 is prepared using synthesis method 2 using intermediates 3g and 5a (yield: 60%)

TLC silica gel 60 F 254 Merck, CH$_2$Cl$_2$-MeOH: 95-5, Rf=0.50.

NMR $^1$H (DMSO-d6) ppm: 10.77 (s, 1H), 8.73 (d, 1H), 8.09 (t, 1H), 8.00 (d, 1H), 7.94 (d, 1H), 7.67 (m, 1H), 7.46 (d, 1H), 7.32 (m, 2H), 7.22 (m, 2H), 7.09 (d, 1H), 3.66 (m, 6H), 3.34 (m, 2H).

MS (−ESI) m/z 512 (M-H−)

Example 12

N-(3-(4-(6-chlorobenzo[d]thiazol-2-yl)piperazine-1-carbonyl)-phenyl)-6-methylpyridine-2-sulfonamide (12)

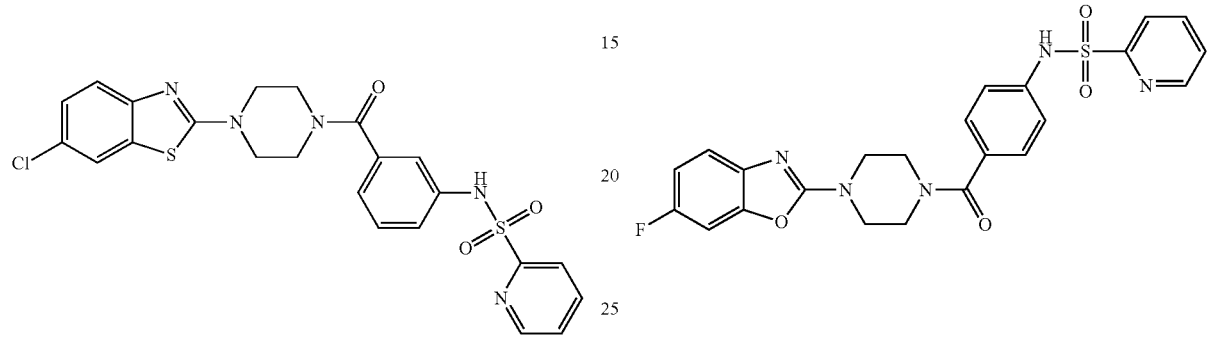

Compound 12 is prepared using synthesis method 2 using intermediates 3g and 5b (yield: 15%).

TLC silica gel 60 F 254 Merck, CH$_2$Cl$_2$-MeOH: 95-5, Rf=0.52.

NMR $^1$H (DMSO-d6) ppm: 10.71 (s, 1H), 7.95 (m, 2H), 7.79 (d, 1H), 7.52 (d, 1H), 7.46 (d, 1H), 7.32 (m, 2H), 7.23 (m, 2H), 7.09 (d, 1H), 3.62 (m, 6H), 3.38 (m, 2H), 2.52 (s, 3H).

MS (+ESI) m/z 528 (MH+)

Beginning of page, before Example 11:

TLC silica gel 60 F 254 Merck, CH$_2$Cl$_2$—AcOEt: 95-5, Rf=0.30.

NMR $^1$H (DMSO-d6) ppm: 10.76 (s, 1H), 8.73 (d, 1H), 8.08 (t, 1H), 8.00 (d, 1H), 7.67 (t, 1H), 7.60 (s, 1H), 7.32 (m, 2H), 7.22 (m, 3H), 7.08 (d, 1H), 3.63 (m, 6H), 3.34 (m, 2H).

MS (+ESI) m/z 498 (MH+)

Example 13

N-(4-(4-(6-fluorobenzo[d]oxazol-2-yl)piperazine-1-carbonyl)phenyl)pyridine-2-sulfonamide (13)

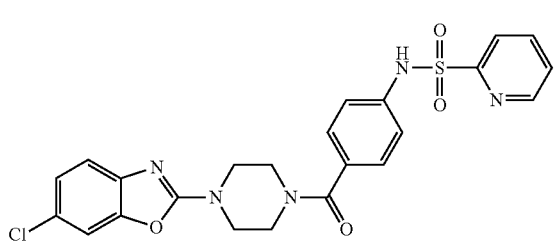 [SMILES: O=C(c1ccc(NS(=O)(=O)c2ccccn2)cc1)N1CCN(c2nc3ccc(Cl)cc3o2)CC1]

Compound 13 is prepared using synthesis method 2 using intermediates 3a and 5c (yield: 53%).

TLC silica gel 60 F 254 Merck, CH$_2$Cl$_2$-MeOH: 95-5, Rf=0.28.

NMR $^1$H (DMSO-d6) ppm: 10.87 (s, 1H), 8.72 (d, 1H), 8.06 (m, 2H), 7.67 (m, 1H), 7.44 (d, 1H), 7.33 (d, 1H), 7.27 (m, 3H), 7.21 (d, 1H), 7.02 (t, 1H), 3.61 (m, 8H).

MS (+ESI) m/z 482 (MH+)

Example 14

N-(4-(4-(6-chlorobenzo[d]oxazol-2-yl)piperazine-1-carbonyl)phenyl)pyridine-2-sulfonamide (14)

Compound 14 is prepared using synthesis method 2 using intermediates 3b and 5c (yield: 56%).

TLC silica gel 60 F 254 Merck, CH$_2$Cl$_2$-MeOH: 95-5, Rf=0.40.

NMR $^1$H (DMSO-d6) ppm: 10.89 (s, 1H), 8.70 (d, 1H), 8.04 (m, 2H), 7.62 (m, 2H), 7.29 (m, 3H), 7.18 (m, 3H), 3.62 (m, 8H).

MS (+ESI) m/z 498 (MH+)

Example 15

N-(4-(4-(6-chlorobenzo[d]thiazol-2-yl)piperazine-1-carbonyl)-phenyl)pyridine-2-sulfonamide (15)

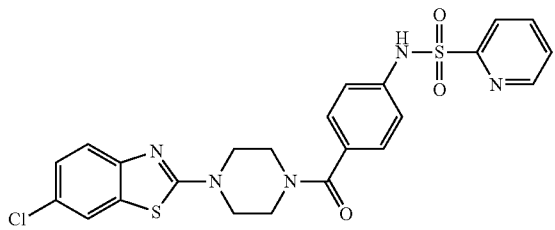

Compound 15 is prepared using synthesis method 2 using intermediates 3g and 5c (yield: 80%).
TLC silica gel 60 F 254 Merck, CH$_2$Cl$_2$-MeOH: 95-5, Rf=0.34.
NMR $^1$H (DMSO-d6) ppm: 10.87 (s, 1H), 8.73 (d, 1H), 8.07 (m, 2H), 7.93 (d, 1H), 7.65 (t, 1H), 7.44 (d, 1H), 7.32 (m, 3H), 7.21 (d, 2H), 3.60 (m, 8H).
MS (−ESI) m/z 512 (M-H−)

Example 16

N-(2-(4-(6-bromobenzo[d]thiazol-2-yl)piperazine-1-carbonyl)phenyl)-quinoline-8-sulfonamide (16)

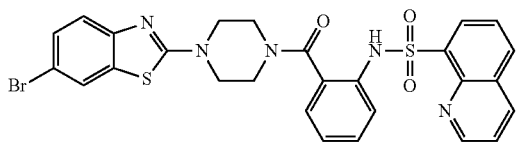

Compound 16 is prepared using synthesis method 1 using intermediate 3f for the first step (yield: 97%) and quinoline-8-sulfonyl chloride for the second step (yield: 61%).
TLC silica gel 60 F 254 Merck, CH$_2$Cl$_2$-MeOH: 95-5, Rf=0.73.
NMR $^1$H (CDCl$_3$) ppm: 9.16 (m, 2H), 8.39 (d, 1H), 8.17 (d, 1H), 7.93 (d, 1H), 7.75 (s, 1H), 7.58 (m, 3H), 7.42 (s, 2H), 7.31 (m, 1H), 7.10 (d, 2H), 3.30 (m, 8H).
MS (+ESI) m/z 608 (MH+)

Example 17

N-(2-(4-(6-chlorobenzo[d]oxazol-2-yl)piperazine-1-carbonyl)-phenyl)quinoline-8-sulfonamide (17)

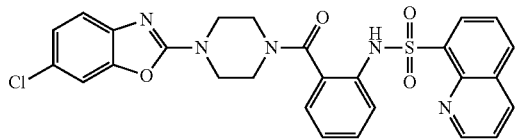

Compound 17 is prepared using synthesis method 1 using intermediate 3b for the first step (yield: 73%) and quinoline-8-sulfonyl chloride for the second step (yield: 50%).
TLC silica gel 60 F 254 Merck, CH$_2$Cl$_2$-MeOH: 95-5, Rf=0.68.
NMR $^1$H (CDCl$_3$) ppm: 9.15 (m, 2H), 8.40 (d, 1H), 8.20 (d, 1H), 7.96 (d, 1H), 7.57 (m, 3H), 7.31 (m, 3H), 7.18 (d, 1H), 7.10 (d, 2H), 3.30 (m, 8H).
MS (+ESI) m/z 548 (MH+)

Example 18

N-(2-(4-(6-chlorobenzo[d]thiazol-2-yl)piperazine-1-carbonyl)-phenyl)quinoline-8-sulfonamide (18)

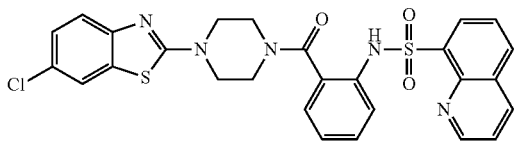 [SMILES: O=C(c1ccccc1NS(=O)(=O)c1cccc2cccnc12)N1CCN(c2nc3ccc(Cl)cc3o2)CC1]

Compound 18 is prepared using synthesis method 1 using intermediate 3g for the first step (yield: 94%) and quinoline-8-sulfonyl chloride for the second step (yield: 82%).
TLC silica gel 60 F 254 Merck, CH$_2$Cl$_2$-MeOH: 95-5, Rf=0.61.
NMR $^1$H (CDCl$_3$) ppm: 9.15 (m, 2H), 8.39 (d, 1H), 8.17 (d, 1H), 7.93 (d, 1H), 7.58 (m, 4H), 7.47 (d, 1H), 7.30 (m, 2H), 7.10 (d, 2H), 3.30 (m, 8H).
MS (+ESI) m/z 564 (MH+)

Example 19

N-(2-(4-(6-(trifluoromethoxy)benzo[d]thiazol-2-yl)piperazine-1-carbonyl)phenyl)quinoline-8-sulfonamide (19)

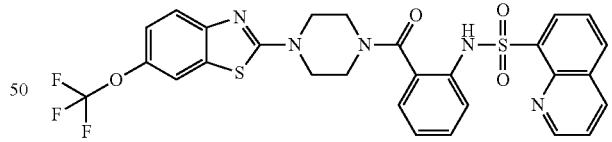

Compound 19 is prepared using synthesis method 1 using intermediate 3i for the first step (yield: 91%) and quinoline-8-sulfonyl chloride for the second step (yield: 67%).
TLC silica gel 60 F 254 Merck, CH$_2$Cl$_2$-MeOH: 95-5, Rf=0.76.
NMR $^1$H (DMSO-d6) ppm: 9.39 (s, 1H), 9.10 (d, 1H), 8.49 (d, 1H), 8.26 (t, 2H), 7.97 (s, 1H), 7.71 (m, 2H), 7.54 (d, 1H), 7.47 (d, 1H), 7.37 (m, 1H), 7.27 (m, 2H), 7.14 (m, 1H), 3.62 (m, 6H), 2.77 (m, 2H).
MS (+ESI) m/z 614 (MH+)

Example 20

N-(2-(4-(4-methylbenzo[d]thiazol-2-yl)-1,4-diazepane-1-carbonyl)-phenyl)quinoline-8-sulfonamide (20)

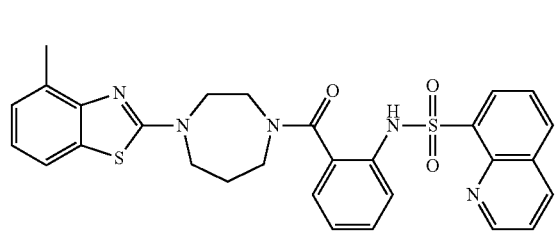 [SMILES: Cc1cccc2sc(N3CCCN(C(=O)c4ccccc4NS(=O)(=O)c4cccc5cccnc45)CC3)nc12]

Compound 20 is prepared using synthesis method 1 using intermediate 3j for the first step (quantitative yield) and quinoline-8-sulfonyl chloride for the second step (yield: 58%).

TLC silica gel 60 F 254 Merck, CH$_2$Cl$_2$-MeOH: 95-5, Rf=0.80.

NMR $^1$H (CDCl$_3$) ppm: 9.13 (m, 1H), 8.86 (m, 1H), 8.62 (d, 1H), 8.41 (m, 1H), 8.20 (m, 1H), 7.98 (m, 1H), 7.55 (m, 2H), 7.47 (m, 1H), 7.28 (m, 1H), 7.12 (m, 1H), 6.99 (m, 2H), 6.85 (m, 1H), 3.71 (m, 4H), 3.51 (m, 2H), 3.20 (m, 2H), 2.47 (s, 3H), 2.09 (m, 2H).

MS (+ESI) m/z 558 (MH+)

Example 21

N-(2-(1-(6-methylbenzo[d]oxazol-2-yl)piperidin-4-yloxy)phenyl)pyridine-2-sulfonamide (21)

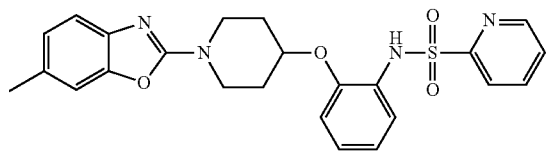 [SMILES: Cc1ccc2nc(N3CCC(Oc4ccccc4NS(=O)(=O)c4ccccn4)CC3)oc2c1]

Compound 21 is prepared using synthesis method 3: intermediate 2e (0.21 g, 1.25 mmol) and intermediate 6a are placed in 5 mL of EtOH in the presence of 0.3 g (3.58 mmol) of sodium bicarbonate, and the mixture is then stirred for 2 h at 80° C. After evaporation under reduced pressure the residue is taken up by water and extracted using AcOEt. After drying of the organic phases and reduction to dryness the residue obtained is triturated in a mixture of EtOH/Et$_2$O and 0.32 g of solid is isolated by filtration (yield: 77%).

TLC silica gel 60 F 254 Merck, CH$_2$Cl$_2$—AcOEt: 70-30, Rf=0.43.

NMR $^1$H (DMSO-d6) ppm: 9.57 (s, 1H), 8.61 (d, 1H), 7.96 (dt, 1H), 7.82 (d, 1H), 7.53 (m, 1H), 7.28 (dd, 1H), 7.24 (s, 1H), 7.18 (d, 1H), 7.11 (t, 1H), 6.98 (m, 2H), 6.86 (t, 1H), 4.53 (m, 1H), 3.72 (m, 2H), 3.48 (m, 2H), 2.35 (s, 3H), 1.77 (m, 2H), 1.48 (m, 2H).

MS (+ESI) m/z 465 (MH+)

Example 22

N-(2-(1-(6-chlorobenzo[d]oxazol-2-yl)piperidin-4-yloxy)phenyl)-pyridine-2-sulfonamide (22)

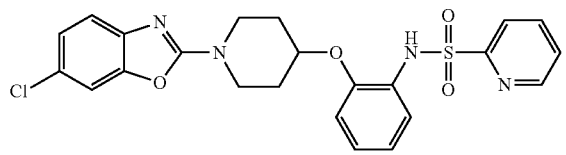 [SMILES: O=S(=O)(Nc1ccccc1OC1CCN(c2nc3ccc(Cl)cc3o2)CC1)c1ccccn1]

Compound 22 is prepared using synthesis method 3 using intermediates 2f and 6a (yield: 83%).

TLC silica gel 60 F 254 Merck, Petroleum ether-AcOEt: 70-30, Rf=0.46.

NMR $^1$H (DMSO-d6) ppm: 9.58 (s, 1H), 8.63 (d, 1H), 7.98 (dt, 1H), 7.83 (d, 1H), 7.59 (d, 1H), 7.55 (m, 1H), 7.28 (m, 2H), 7.20 (dd, 1H), 7.14 (t, 1H), 6.99 (d, 1H), 6.86 (t, 1H), 4.54 (m, 1H), 3.72 (m, 2H), 3.52 (m, 2H), 1.79 (m, 2H), 1.51 (m, 2H).

MS (+ESI) m/z 485 (MH+)

Example 23

N-(2-(1-(5-tert-butylbenzo[d]oxazol-2-yl)piperidin-4-yloxy)phenyl)pyridine-2-sulfonamide (23)

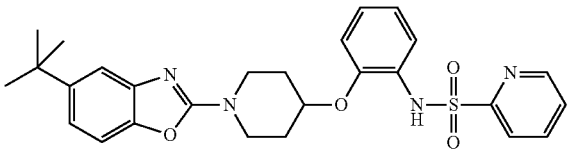 [SMILES: CC(C)(C)c1ccc2oc(N3CCC(Oc4ccccc4NS(=O)(=O)c4ccccn4)CC3)nc2c1]

Compound 23 is prepared using synthesis method 3 using intermediates 2g and 6a (yield: 82%).

TLC silica gel 60 F 254 Merck, CH$_2$Cl$_2$-MeOH: 90-10, Rf=0.65.

NMR $^1$H (DMSO-d6) ppm: 9.57 (s, 1H), 8.63 (m, 1H), 7.97 (dt, 1H), 7.83 (d, 1H), 7.53 (m, 1H), 7.30 (m, 3H), 7.11 (dt, 1H), 7.05 (dd, 1H), 6.99 (d, 1H), 6.85 (dt, 1H), 4.54 (m, 1H), 3.74 (m, 2H), 3.50 (m, 2H), 1.78 (m, 2H), 1.48 (m, 2H), 1.30 (s, 9H).

MS (+ESI) m/z 507 (MH+)

Example 24

N-(2-(1-(5-chlorobenzo[d]oxazol-2-yl)piperidin-4-yloxy)phenyl)-pyridine-2-sulfonamide (24)

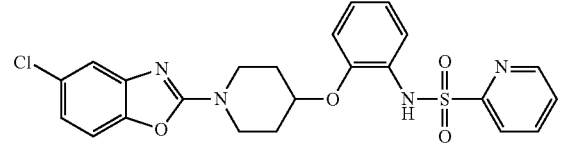 [SMILES: O=S(=O)(Nc1ccccc1OC1CCN(c2nc3cc(Cl)ccc3o2)CC1)c1ccccn1]

Compound 24 is prepared using synthesis method 3 using intermediates 2h and 6a (yield: 92%).

TLC silica gel 60 F 254 Merck, CH$_2$Cl$_2$—AcOEt: 70-30, Rf=0.33.

NMR $^1$H (DMSO-d6) ppm: 9.57 (s, 1H), 8.63 (d, 1H), 7.98 (dt, 1H), 7.83 (d, 1H), 7.55 (m, 1H), 7.43 (d, 1H), 7.35 (d, 1H), 7.29 (dd, 1H), 7.12 (t, 1H), 7.04 (dd, 1H), 6.99 (d, 1H), 6.86 (t, 1H), 4.55 (m, 1H), 3.74 (m, 2H), 3.55 (m, 2H), 1.79 (m, 2H), 1.52 (m, 2H).

MS (+ESI) m/z 485 (MH+)

Example 25

N-(2-(1-(benzo[d]thiazol-2-yl)piperidin-4-yloxy)phenyl)pyridine-2-sulfonamide (25)

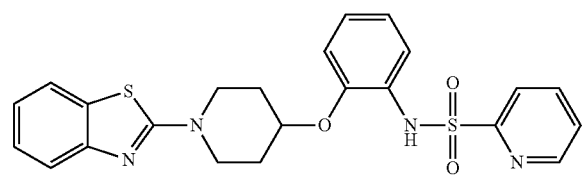 [SMILES: O=S(=O)(Nc1ccccc1OC1CCN(c2nc3ccccc3s2)CC1)c1ccccn1]

Compound 25 is prepared using synthesis method 3 using intermediate 6a and 2-chloro-1,3-benzothiazole (yield: 81%).

TLC silica gel 60 F 254 Merck, CH$_2$Cl$_2$—AcOEt: 80-20, Rf=0.75.

NMR $^1$H (DMSO-d6) ppm: 9.59 (s, 1H), 8.62 (d, 1H), 7.97 (dt, 1H), 7.82 (d, 1H), 7.77 (d, 1H), 7.53 (m, 1H), 7.47 (d, 1H), 7.28 (m, 2H), 7.10 (m, 2H), 6.99 (d, 1H), 6.86 (t, 1H), 4.56 (m, 1H), 3.72 (m, 2H), 3.47 (m, 2H), 1.79 (m, 2H), 1.53 (m, 2H).

MS (+ESI) m/z 467 (MH+)

Example 26

N-(2-(1-(6-chlorobenzo[d]thiazol-2-yl)piperidin-4-yloxy)phenylpyridine-2-sulfonamide (26)

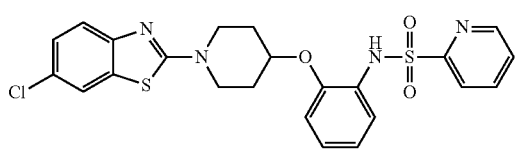 [SMILES: O=S(=O)(Nc1ccccc1OC1CCN(c2nc3ccc(Cl)cc3s2)CC1)c1ccccn1]

Compound 26 is prepared using synthesis method 3 using intermediate 6a and 2,6-dichloro-1,3-benzothiazole (yield: 82%).

TLC silica gel 60 F 254 Merck, Petroleum ether-AcOEt: 60-40, Rf=0.20.

NMR $^1$H (DMSO-d6) ppm: 9.59 (s, 1H), 8.62 (d, 1H), 7.97 (dt, 1H), 7.91 (d, 1H), 7.82 (d, 1H), 7.54 (m, 1H), 7.44 (d, 1H), 7.29 (m, 2H), 7.12 (t, 1H), 6.99 (d, 1H), 6.86 (t, 1H), 4.56 (m, 1H), 3.72 (m, 2H), 3.49 (m, 2H), 1.78 (m, 2H), 1.52 (m, 2H).

MS (+ESI) m/z 501 (MN+)

Example 27

N-(2-(1-(6-bromobenzo[d]thiazol-2-yl)piperidin-4-yloxy)phenyl)-pyridine-2-sulfonamide (27)

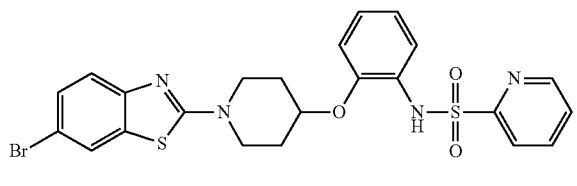 [SMILES: O=S(=O)(Nc1ccccc1OC1CCN(c2nc3ccc(Br)cc3s2)CC1)c1ccccn1]

Compound 27 is prepared using synthesis method 3 using intermediates 2d and 6a (yield: 14%).

TLC silica gel 60 F 254 Merck, Petroleum ether-AcOEt: 60-40, Rf=0.21.

NMR $^1$H (DMSO-d6) ppm: 9.59 (s, 1H), 8.62 (d, 1H), 8.03 (t, 1H), 7.98 (t, 1H), 7.82 (d, 1H), 7.53 (m, 1H), 7.40 (m, 2H), 7.26 (d, 1H), 7.12 (t, 1H), 6.99 (d, 1H), 6.86 (t, 1H), 4.56 (m, 1H), 3.72 (m, 2H), 3.49 (m, 2H), 1.79 (m, 2H), 1.53 (m, 2H).

MS (+ESI) m/z 545 (MN+)

Example 28

N-(2-((1-(benzo[d]thiazol-2-yl)pyrrolidin-3-yl)methoxy)phenyl)-pyridine-2-sulfonamide (28)

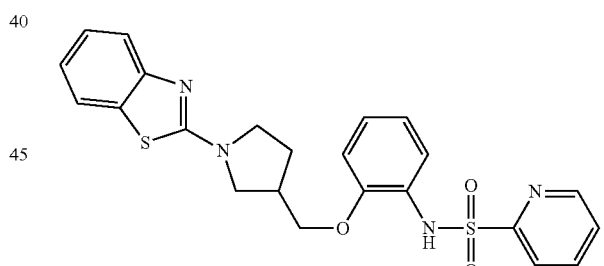

Compound 28 is prepared using synthesis method 3 using intermediate 6b and 2-chloro-1,3-benzothiazole (yield: 66%).

TLC silica gel 60 F 254 Merck, CH$_2$Cl$_2$-MeOH: 90-10, Rf=0.44.

NMR $^1$H (DMSO-d6) ppm: 9.62 (s, 1H), 8.73 (d, 1H), 8.03 (dt, 1H), 7.76 (d, 1H), 7.64 (m, 1H), 7.46 (d, 1H), 7.28 (m, 2H), 7.12 (dt, 2H), 7.03 (t, 1H), 6.94 (d, 1H), 6.86 (t, 1H), 3.81 (d, 2H), 3.68 (m, 1H), 3.56 (m, 1H), 3.48 (m, 1H), 3.30 (m, 1H), 2.61 (m, 1H), 2.12 (m, 1H), 1.85 (m, 1H).

MS (+ESI) m/z 467 (MH+)

Example 29

N-(2-((1-(6-fluorobenzo[d]thiazol-2-yl)pyrrolidin-3-yl)methoxy)phenyl)pyridine-2-sulfonamide (29)

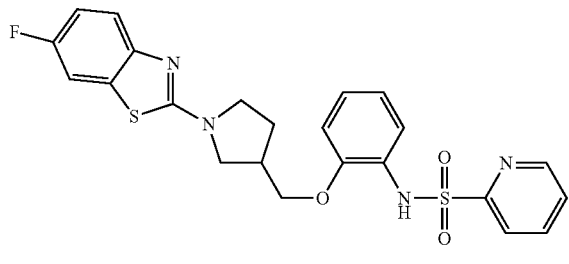 [SMILES: O=S(=O)(Nc1ccccc1OCC1CCN(c2nc3ccc(F)cc3s2)C1)c1ccccn1]

Compound 29 is prepared using synthesis method 3 using intermediates 2a and 6b (yield: 76%).

TLC silica gel 60 F 254 Merck, AcOEt, Rf=0.55.

NMR $^1$H (DMSO-d6) ppm: 9.61 (s, 1H), 8.72 (d, 1H), 8.03 (t, 1H), 7.84 (d, 1H), 7.71 (d, 1H), 7.63 (m, 1H), 7.45 (m, 1H), 7.26 (d, 1H), 7.12 (m, 2H), 6.94 (d, 1H), 6.86 (t, 1H), 3.83 (d, 2H), 3.67 (m, 1H), 3.53 (m, 1H), 3.48 (m, 1H), 3.30 (m, 1H), 2.62 (m, 1H), 2.09 (m, 1H), 1.85 (m, 1H).

MS (+ESI) m/z 485 (MH+)

Example 30

N-(2-((1-(6-chlorobenzo[d]thiazol-2-yl)pyrrolidin-3-yl)methoxy)phenyl)pyridine-2-sulfonamide (30)

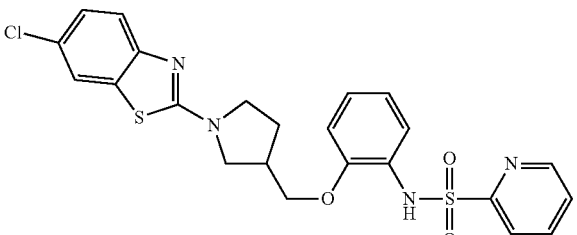

Compound 30 is prepared using synthesis method 3 using intermediate 6b and 2,6-dichloro-1,3-benzothiazole (yield: 80%).

TLC silica gel 60 F 254 Merck, Petroleum ether-AcOEt: 50-50, Rf=0.23.

NMR $^1$H (DMSO-d6) ppm: 9.61 (s, 1H), 8.72 (d, 1H), 8.03 (dt, 1H), 7.91 (d, 1H), 7.84 (d, 1H), 7.63 (m, 1H), 7.43 (d, 1H), 7.28 (m, 2H), 7.10 (t, 1H), 6.94 (d, 1H), 6.86 (t, 1H), 4.03 (d, 2H), 3.66 (m, 1H), 3.53 (m, 2H), 3.30 (m, 1H), 2.61 (m, 1H), 2.11 (m, 1H), 1.84 (m, 1H).

MS (+ESI) m/z 501 (MH+)

Example 31

N-(2-((1-(4-methylbenzo[d]thiazol-2-yl)pyrrolidin-3-yl)methoxy)phenyl)pyridine-2-sulfonamide (31)

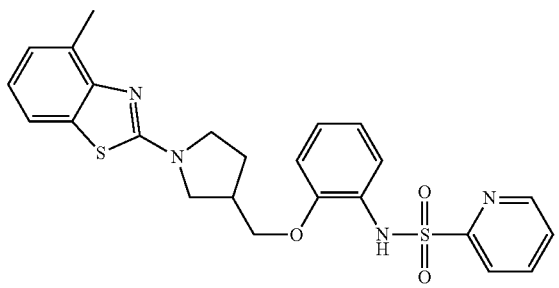 [SMILES: Cc1cccc2sc(N3CCC(COc4ccccc4NS(=O)(=O)c4ccccn4)C3)nc12]

Compound 31 is prepared using synthesis method 3 using intermediates 2b and 6b (yield: 28%).

TLC silica gel 60 F 254 Merck, Petroleum ether-AcOEt: 50-50, Rf=0.36.

NMR $^1$H (DMSO-d6) ppm: 9.61 (s, 1H), 8.74 (d, 1H), 8.04 (t, 1H), 7.84 (d, 1H), 7.63 (m, 1H), 7.57 (d, 1H), 7.28 (d, 1H), 7.10 (m, 2H), 6.94 (m, 2H), 6.86 (t, 1H), 3.84 (d, 2H), 3.72 (m, 1H), 3.58 (m, 1H), 3.52 (m, 1H), 3.30 (m, 1H), 2.63 (m, 1H), 2.5 (s, 3H), 2.10 (m, 1H), 1.80 (m, 1H).

MS (+ESI) m/z 481 (MH+)

Example 32

N-(2-((1-(4-methoxybenzo[d]thiazol-2-yl)pyrrolidin-3-yl)methoxy)-phenyl)pyridine-2-sulfonamide (32)

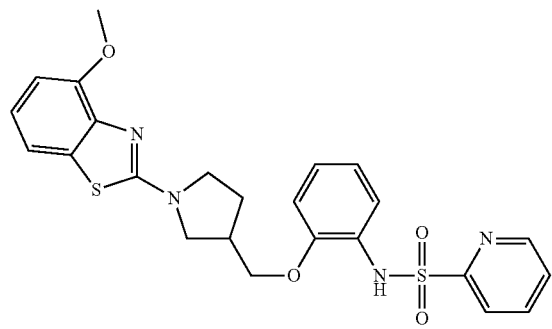 [SMILES: COc1cccc2sc(N3CCC(COc4ccccc4NS(=O)(=O)c4ccccn4)C3)nc12]

Compound 32 is prepared using synthesis method 3 using intermediates 2c and 6b (yield: 51%).

TLC silica gel 60 F 254 Merck, Petroleum ether-AcOEt: 50-50, Rf=0.63.

NMR $^1$H (DMSO-d6) ppm: 9.61 (s, 1H), 8.76 (d, 1H), 8.05 (t, 1H), 7.84 (d, 1H), 7.63 (m, 1H), 7.34 (d, 1H), 7.28 (d, 1H), 7.10 (t, 1H), 7.00 (t, 1H), 6.94 (d, 1H), 6.89 (m, 2H), 3.86 (s, 3H), 3.82 (d, 2H), 3.67 (m, 1H), 3.50 (m, 2H), 3.27 (m, 1H), 2.63 (m, 1H), 2.10 (m, 1H), 1.83 (m, 1H).

MS (+ESI) m/z 497 (MH+)

Example 33 lithium N-(2-(4-(6-bromobenzo[d]thiazol-2-yl)piperazine-1-carbonyl)phenyl)-pyridine-2-sulfonamide (33)

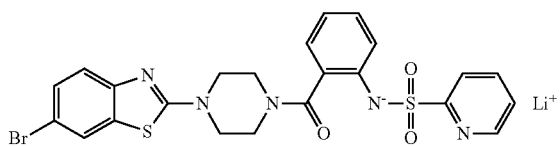

2.36 g (4.23 mmol) of compound 3 prepared according to example 3 are added to 30 mL of ethanol. Then, a 1M solution of LiOH (4.23 mL, 4.23 mmol) is added and the mixture is stirred for 30 min at room temperature. The solvent is concentrated until dryness; the residue is taken up in diethyl ether and stirred for 2 h at room temperature. After filtration, compound 33 (2.45 g) is isolated in the form of a solid and then dried under vacuum.

mp=122.42° C.

NMR $^1$H (DMSO-d6) ppm: 8.48 (d, 1H), 8.03 (s, 1H), 7.81 (d, 2H), 7.38 (m 2H), 7.38 (m, 1H), 7.18 (d, 1H), 6.86 (m, 2H), 6.46 (t, 1H), 4.02 (m, 2H), 3.78 (m, 1H), 3.44 (m, 4H), 3.14 (m, 1H).

MS (+ESI) m/z 558 (MH+)

Example 34 sodium N-(2-(4-(6-bromobenzo[d]thiazol-2-yl)piperazine-1-carbonyl)phenyl)-pyridine-2-sulfonamide (34)

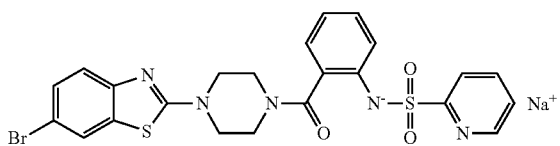 [SMILES: O=C(c1ccccc1[N-]S(=O)(=O)c1ccccn1)N1CCN(c2nc3ccc(Br)cc3s2)CC1 ; [Na+]]

Compound 34 is prepared using synthesis method described in example 33 using a 1M solution of NaOH. After filtration, compound 34 (2.46 g) is isolated in the form of a solid and then dried under vacuum.

mp=330° C.

NMR $^1$H (DMSO-d6) ppm: 8.48 (d, 1H), 8.03 (s, 1H), 7.82 (m, 2H), 7.39 (m 2H), 7.34 (m, 1H), 7.17 (d, 1H), 6.86 (m, 2H), 6.46 (t, 1H), 4.01 (m, 2H), 3.78 (m, 1H), 3.46 (m, 4H), 3.14 (m, 1H).

MS (+ESI) m/z 558 (MH+)

Example 35

Potassium N-(2-(4-(6-bromobenzo[d]thiazol-2-yl)piperazine-1-carbonyl)phenyl)-pyridine-2-sulfonamide (35)

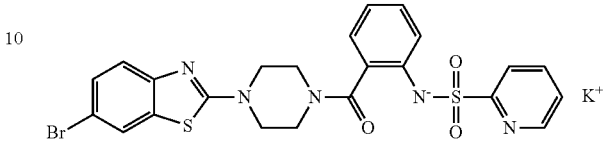

Compound 35 is prepared using synthesis method described in example 33 using a 1M solution of KOH. After filtration, compound 35 (2.51 g) is isolated in the form of a solid and then dried under vacuum.

mp=201° C.

NMR $^1$H (DMSO-d6) ppm: 8.49 (d, 1H), 8.03 (s, 1H), 7.82 (m, 2H), 7.39 (m 2H), 7.34 (m, 1H), 7.18 (d, 1H), 6.87 (m, 2H), 6.46 (t, 1H), 4.00 (m, 2H), 3.78 (m, 1H), 3.42 (m, 4H), 3.14 (m, 1H).

MS (+ESI) m/z 558 (MH+)

C) Pharmacological Evaluation

The pharmacological evaluation of the compounds on potassium channel Kv1.5 was undertaken using a 96-well plate and FLIPR technology by thallium ion measurement. The HEK293 cells, transfected in a stable manner with the human isoform of the Kv1.5 channels, are seeded 24 h before the experiment in 96-well plates (15 $10^8$ cells/plate, 200 μl/well) with polylysine applied in the following culture medium: DMEM, 10% SVF, Penicillin/Streptomycin, G418 as the selection antibiotic.

The FLIPR experiment is undertaken using "FLIPR Potassium Ion Channel Assay Kit", as indicated by the manufacturer (Molecular Devices).

Briefly, the culture medium is replaced by the solution containing the thallium marker for 90 min at 37° C. On conclusion of this step the compounds for testing are added to a final concentration of 10 μM in the well for 15 min at 37° C. The basic fluorescence is then read for 60 sec. The addition of depolarising medium (20 mM of potassium and 3 mM of final thallium) opens the potassium channels and causes an increase of the fluorescence of the thallium fluorophore corresponding to an influx of thallium ions through the hKv1.5 channels. The measurement is made 30 sec after the injection of the depolarising solution. The application of 10 μM DPO (Tocris, blocker of the Kv1.5 channels) enables the fluorescence to be normalised.

TABLE 1

| Examples | % inhibition at 10 μM |
|---|---|
| BMS394136* | 99.6 |
| 1 | 61.4 |
| 2 | 100 |
| 3 | 100 |
| 4 | 100 |
| 5 | 90 |
| 6 | 91.8 |
| 7 | 94.9 |
| 8 | 94.7 |
| 9 | 62.8 |
| 10 | 58.9 |

TABLE 1-continued

| Examples | % inhibition at 10 μM |
|---|---|
| 11 | 75.1 |
| 12 | 52.6 |
| 13 | 100 |
| 14 | 68.7 |
| 15 | 70.2 |
| 16 | 68 |
| 17 | 70.8 |
| 18 | 91.5 |
| 19 | 50.2 |
| 20 | 82.8 |
| 21 | 54.6 |
| 22 | 58.8 |
| 23 | 51.8 |
| 24 | 81.0 |
| 25 | 90.2 |
| 26 | 65.8 |
| 27 | 100 |
| 28 | 76.0 |
| 29 | 64.5 |
| 30 | 54.1 |
| 31 | 56.0 |
| 32 | 53.7 |

*BMS394136 is a blocker of the Kv1.5 channel under development at Bristol-Myers Squibb (Abstract, D. Xing et al., Circulation 2009, 120 (18S3): 2515).

The results obtained show that compounds of general formula (I) block channel Kv1.5. Compounds of general formula I can be used as blockers of channel Kv1.5.

D) Abbreviations

DEAD Diethyl azodicarboxylate
DMAP N,N-4-Dimethylaminopyridine
DMF Dimethylformamide
DMSO Dimethyl sulfoxide
DPO (2-isopropyl-5-methyl-cyclohexyl)diphenylphosphine oxide
ESI Electrospray ionisation
HPLC High-performance liquid chromatography
mp Melting point
MS Mass spectrum
NMR Nuclear magnetic resonance
Rf Retardation factor
Temp. Temperature
TFA Trifluoroacetic acid
THF Tetrahydrofuran
TLC Thin Layer Chromatography

The invention claimed is:

1. A method for blocking Kv potassium channels comprising the administration to a person in need thereof of an effective amount of a compound of general formula Ia:

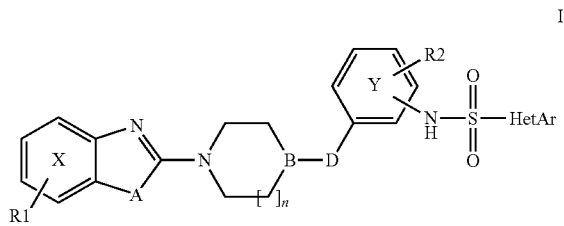

where
R1 represents one or more substituents of the phenyl core X chosen from among the group consisting of: hydrogen, halogen, trifluoromethyl, trifluoromethoxy, linear or branched $C_1$-$C_4$ alkyl, and linear or branched $C_1$-$C_4$ alkoxy,
n represents 0, 1 or 2,
A represents oxygen or sulphur,
D represents —C(=O)—, —CH$_2$O— or —O—,
B represents nitrogen when n is 1 or 2 and D represents —C(=O)—, or
B represents CH when n is 0 and D represents —CH$_2$O— or when n is 1 and D represents —O—,
R2 represents a substituent of phenyl core Y selected from a hydrogen, a methyl, a fluorine atom, a chlorine atom and a methoxy, and
HetAr represents a pyridyl or quinolyl group, possibly substituted with a group selected from a linear or branched $C_1$-$C_4$ alkyl, a linear or branched $C_1$-$C_4$ alkoxy, a halogen, and trifluoromethyl,
or one of its pharmaceutically acceptable salts.

2. The method according to claim 1, wherein:
R1 represents one or more substituents of the phenyl core X chosen from among the group consisting of: hydrogen, halogen, trifluoromethyl, trifluoromethoxy, linear or branched $C_1$-$C_4$ alkyl, and methoxy,
n represents 1,
D represents —C(=O)— or —O—,
B represents nitrogen when D represents —C(=O)—,
or B represents CH when D represents —O—,
R2 represents a hydrogen, and
HetAr represents a 2-pyridyl or 8-quinolyl group, possibly substituted with a group selected from methyl and trifluoromethyl.

3. The method according to claim 1, wherein:
R1 represents one or more substituents of the phenyl core X chosen from among the group consisting of: hydrogen, halogen, trifluoromethyl, trifluoromethoxy, linear or branched $C_1$-$C_4$ alkyl, or methoxy,
A represents sulphur,
n represents 1,
D represents —C(=O)—,
B represents nitrogen,
R2 represents a hydrogen, and
HetAr represents a 2-pyridyl group, possibly substituted with a group selected from methyl and trifluoromethyl.

4. The method according to claim 1, wherein the compound of formula Ia is selected from:
1) N-(2-(4-(6-fluorobenzo[d]oxazol-2-yl)piperazine-1-carbonyl)phenyl)-5-(trifluoromethyl)pyridine-2-sulfonamide,
2) N-(2-(4-(6-fluorobenzo[d]thiazol-2-yl)piperazine-1-carbonyl)phenyl)pyridine-2-sulfonamide,
3) N-(2-(4-(6-bromobenzo[d]thiazol-2-yl)piperazine-1-carbonyl)phenyl)pyridine-2-sulfonamide,
4) N-(2-(4-(6-chlorobenzo[d]thiazol-2-yl)piperazine-1-carbonyl)phenyl)-pyridine-2-sulfonamide hydrochloride,
5) N-(2-(4-(4-methylbenzo[d]thiazol-2-yl)piperazine-1-carbonyl)phenyl)pyridine-2-sulfonamide,
6) N-(2-(4-(7-chlorobenzo[d]thiazol-2-yl)piperazine-1-carbonyl)-phenyl)pyridine-2-sulfonamide,
7) N-(2-(4-(5-(trifluoromethyl)benzo[d]thiazol-2-yl)piperazine-1-carbonyl)-phenyl)-pyridine-2-sulfonamide,
8) N-(2-(4-(6-chlorobenzo[d]thiazol-2-yl)piperazine-1-carbonyl)phenyl)-5-(trifluoromethyl)pyridine-2-sulfonamide,
9) N-(2-(4-(6-bromobenzo[d]thiazol-2-yl)piperazine-1-carbonyl)phenyl)-6-methylpyridine-2-sulfonamide dihydrochloride, 16) N-(2-(4-(6-bromobenzo[d]thiazol-2-yl)piperazine-1-carbonyl)-phenyl)quinoline-8-sulfonamide,
17) N-(2-(4-(6-chlorobenzo[d]oxazol-2-yl)piperazine-1-carbonyl)-phenyl)quinoline-8-sulfonamide,
18) N-(2-(4-(6-chlorobenzo[d]thiazol-2-yl)piperazine-1-carbonyl)-phenyl)quinoline-8-sulfonamide,
19) N-(2-(4-(6-(trifluoromethoxy)benzo[d]thiazol-2-yl)piperazine-1-carbonyl)-phenyl)quinoline-8-sulfonamide,
20) N-(2-(4-(4-methylbenzo[d]thiazol-2-yl)-1,4-diazepane-1-carbonyl)-phenyl)quinoline-8-sulfonamide,
21) N-(2-(1-(6-methylbenzo[d]oxazol-2-yl)piperidin-4-yloxy)phenyl)-pyridine-2-sulfonamide,
22) N-(2-(1-(6-chlorobenzo[d]oxazol-2-yl)piperidin-4-yloxy)phenyl)pyridine-2-sulfonamide,
23) N-(2-(1-(5-tert-butylbenzo[d]oxazol-2-yl)piperidin-4-yloxy)phenyl)pyridine-2-sulfonamide,
24) N-(2-(1-(5-chlorobenzo[d]oxazol-2-yl)piperidin-4-yloxy)phenyl)pyridine-2-sulfonamide,
25) N-(2-(1-(benzo[d]thiazol-2-yl)piperidin-4-yloxy)phenyl)pyridine-2-sulfonamide,
26) N-(2-(1-(6-chlorobenzo[d]thiazol-2-yl)piperidin-4-yloxy)phenyl-pyridine-2-sulfonamide,
27) N-(2-(1-(6-bromobenzo[d]thiazol-2-yl)piperidin-4-yloxy)phenyl)-pyridine-2-sulfonamide,
28) N-(2-((1-(benzo[d]thiazol-2-yl)pyrrolidin-3-yl)methoxy)phenyl)-pyridine-2-sulfonamide,
29) N-(2-((1-(6-fluorobenzo[d]thiazol-2-yl)pyrrolidin-3-yl)methoxy)phenyl)-pyridine-2-sulfonamide,
30) N-(2-((1-(6-chlorobenzo[d]thiazol-2-yl)pyrrolidin-3-yl)methoxy)phenyl)-pyridine-2-sulfonamide,
31) N-(2-((1-(4-methylbenzo[d]thiazol-2-yl)pyrrolidin-3-yl)methoxy)phenyl)-pyridine-2-sulfonamide,
32) N-(2-((1-(4-methoxybenzo[d]thiazol-2-yl)pyrrolidin-3-yl)methoxy)-phenyl)-pyridine-2-sulfonamide,
33) lithium N-(2-(4-(6-bromobenzo[d]thiazol-2-yl)piperazine-1-carbonyl)phenyl)-pyridine-2-sulfonamide,
34) sodium N-(2-(4-(6-bromobenzo[d]thiazol-2-yl)piperazine-1-carbonyl)phenyl)-pyridine-2-sulfonamide, and
35) potassium N-(2-(4-(6-bromobenzo[d]thiazol-2-yl)piperazine-1-carbonyl)phenyl)-pyridine-2-sulfonamide.

5. The method according to claim 1, wherein the Kv potassium channel is the channel Kv1.5, Kv4.3, or Kv11.1.

6. A method for treating atrial fibrillation, heart rhythm disorders of the auricles and/or the ventricles comprising the administration to a person in need thereof of an effective amount of a compound of general formula Ia:

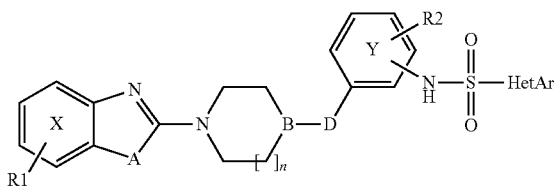

Ia where
R1 represents one or more substituents of the phenyl core X chosen from among the group consisting of: hydrogen, halogen, trifluoromethyl, trifluoromethoxy, linear or branched $C_1$-$C_4$ alkyl, and linear or branched $C_1$-$C_4$ alkoxy, n represents 0, 1 or 2,
A represents oxygen or sulphur,
D represents —C(=O)—, —CH$_2$O— or —O—,
B represents nitrogen when n is 1 or 2 and D represents —C(=O)—, or
B represents CH when n is 0 and D represents —CH$_2$O— or when n is 1 and D represents —O—,
R2 represents a substituent of phenyl core Y selected from a hydrogen, a methyl, a fluorine atom, a chlorine atom and a methoxy, and
HetAr represents a pyridyl or quinolyl group, possibly substituted with a group selected from a linear or branched $C_1$-$C_4$ alkyl, a linear or branched $C_1$-$C_4$ alkoxy, a halogen, and trifluoromethyl, or one of its pharmaceutically acceptable salts.

7. The method according to claim 6, wherein:
R1 represents one or more substituents of the phenyl core X chosen from among the group consisting of: hydrogen, halogen, trifluoromethyl, trifluoromethoxy, linear or branched $C_1$-$C_4$ alkyl, and methoxy,
n represents 1,
D represents —C(=O)— or —O—,
B represents nitrogen when D represents —C(=O)—,
or B represents CH when D represents —O—,
R2 represents a hydrogen, and
HetAr represents a 2-pyridyl or 8-quinolyl group, possibly substituted with a group selected from methyl and trifluoromethyl.

8. The method according to claim 6, wherein:
R1 represents one or more substituents of the phenyl core X chosen from among the group consisting of: hydrogen, halogen, trifluoromethyl, trifluoromethoxy, linear or branched $C_1$-$C_4$ alkyl, or methoxy,
A represents sulphur,
n represents 1,
D represents —C(=O)—,
B represents nitrogen,
R2 represents a hydrogen, and
HetAr represents a 2-pyridyl group, possibly substituted with a group selected from methyl and trifluoromethyl.

9. The method according to claim 6, wherein the compound of formula Ia is selected from:
1) N-(2-(4-(6-fluorobenzo[d]oxazol-2-yl)piperazine-1-carbonyl)phenyl)-5-(trifluoromethyl)pyridine-2-sulfonamide,
2) N-(2-(4-(6-fluorobenzo[d]thiazol-2-yl)piperazine-1-carbonyl)phenyl)pyridine-2-sulfonamide,
3) N-(2-(4-(6-bromobenzo[d]thiazol-2-yl)piperazine-1-carbonyl)phenyl)pyridine-2-sulfonamide,
4) N-(2-(4-(6-chlorobenzo[d]thiazol-2-yl)piperazine-1-carbonyl)phenyl)-pyridine-2-sulfonamide hydrochloride,
5) N-(2-(4-(4-methylbenzo[d]thiazol-2-yl)piperazine-1-carbonyl)phenyl)pyridine-2-sulfonamide,
6) N-(2-(4-(7-chlorobenzo[d]thiazol-2-yl)piperazine-1-carbonyl)-phenyl)pyridine-2-sulfonamide,
7) N-(2-(4-(5-(trifluoromethyl)benzo[d]thiazol-2-yl)piperazine-1-carbonyl)-phenyl)-pyridine-2-sulfonamide,
8) N-(2-(4-(6-chlorobenzo[d]thiazol-2-yl)piperazine-1-carbonyl)phenyl)-5-(trifluoromethyl)pyridine-2-sulfonamide,
9) N-(2-(4-(6-bromobenzo[d]thiazol-2-yl)piperazine-1-carbonyl)phenyl)-6-methylpyridine-2-sulfonamide dihydrochloride,
16) N-(2-(4-(6-bromobenzo[d]thiazol-2-yl)piperazine-1-carbonyl)-phenyl)quinoline-8-sulfonamide, 17) N-(2-(4-(6-chlorobenzo[d]oxazol-2-yl)piperazine-1-carbonyl)-phenyl)quinoline-8-sulfonamide,
18) N-(2-(4-(6-chlorobenzo[d]thiazol-2-yl)piperazine-1-carbonyl)-phenyl)quinoline-8-sulfonamide,
19) N-(2-(4-(6-(trifluoromethoxy)benzo[d]thiazol-2-yl)piperazine-1-carbonyl)-phenyl)quinoline-8-sulfonamide,
20) N-(2-(4-(4-methylbenzo[d]thiazol-2-yl)-1,4-diazepane-1-carbonyl)-phenyl)quinoline-8-sulfonamide,
21) N-(2-(1-(6-methylbenzo[d]oxazol-2-yl)piperidin-4-yloxy)phenyl)-pyridine-2-sulfonamide,
22) N-(2-(1-(6-chlorobenzo[d]oxazol-2-yl)piperidin-4-yloxy)phenyl)pyridine-2-sulfonamide,
23) N-(2-(1-(5-tert-butylbenzo[d]oxazol-2-yl)piperidin-4-yloxy)phenyl)pyridine-2-sulfonamide,
24) N-(2-(1-(5-chlorobenzo[d]oxazol-2-yl)piperidin-4-yloxy)phenyl)pyridine-2-sulfonamide,
25) N-(2-(1-(benzo[d]thiazol-2-yl)piperidin-4-yloxy)phenyl)pyridine-2-sulfonamide,
26) N-(2-(1-(6-chlorobenzo[d]thiazol-2-yl)piperidin-4-yloxy)phenyl-pyridine-2-sulfonamide,
27) N-(2-(1-(6-bromobenzo[d]thiazol-2-yl)piperidin-4-yloxy)phenyl)-pyridine-2-sulfonamide,
28) N-(2-((1-(benzo[d]thiazol-2-yl)pyrrolidin-3-yl)methoxy)phenyl)-pyridine-2-sulfonamide,
29) N-(2-((1-(6-fluorobenzo[d]thiazol-2-yl)pyrrolidin-3-yl)methoxy)phenyl)-pyridine-2-sulfonamide,
30) N-(2-((1-(6-chlorobenzo[d]thiazol-2-yl)pyrrolidin-3-yl)methoxy)phenyl)-pyridine-2-sulfonamide,
31) N-(2-((1-(4-methylbenzo[d]thiazol-2-yl)pyrrolidin-3-yl)methoxy)phenyl)-pyridine-2-sulfonamide,
32) N-(2-((1-(4-methoxybenzo[d]thiazol-2-yl)pyrrolidin-3-yl)methoxy)-phenyl)-pyridine-2-sulfonamide,
33) lithium N-(2-(4-(6-bromobenzo[d]thiazol-2-yl)piperazine-1-carbonyl)phenyl)-pyridine-2-sulfonamide,
34) sodium N-(2-(4-(6-bromobenzo[d]thiazol-2-yl)piperazine-1-carbonyl)phenyl)-pyridine-2-sulfonamide, and
35) potassium N-(2-(4-(6-bromobenzo[d]thiazol-2-yl)piperazine-1-carbonyl)phenyl)-pyridine-2-sulfonamide.

* * * * *